United States Patent
Couture et al.

(10) Patent No.: US 7,857,821 B2
(45) Date of Patent: Dec. 28, 2010

(54) SURGICAL UNIVERSAL POSITIONING BLOCK AND TOOL GUIDE

(75) Inventors: Pierre Couture, Montréal (CA); Benoit Pelletier, Montréal (CA); Alain Richard, Montréal (CA); Jean-Guillaume Abiven, Montréal (CA); Patrick Garceau, Montréal (CA)

(73) Assignee: Orthosoft Inc., Montreal, Quebec (CA)

( * ) Notice: Subject to any disclaimer, the term of this patent is extended or adjusted under 35 U.S.C. 154(b) by 97 days.

(21) Appl. No.: 11/936,854

(22) Filed: Nov. 8, 2007

(65) Prior Publication Data
US 2008/0065085 A1 Mar. 13, 2008

Related U.S. Application Data

(60) Division of application No. 11/062,737, filed on Feb. 23, 2005, now Pat. No. 7,736,368, which is a continuation of application No. PCT/CA03/01307, filed on Aug. 25, 2003.

(60) Provisional application No. 60/405,353, filed on Aug. 23, 2002, provisional application No. 60/405,326, filed on Aug. 23, 2002.

(51) Int. Cl.
*A61F 5/00* (2006.01)
(52) U.S. Cl. .................. 606/130; 606/88; 606/86 R
(58) Field of Classification Search ......... 606/86 R–89, 606/130, 96, 97, 102, 104
See application file for complete search history.

(56) References Cited

U.S. PATENT DOCUMENTS

| | | | |
|---|---|---|---|
| 4,710,075 A | 12/1987 | Davison | |
| 4,712,542 A | 12/1987 | Daniel et al. | |
| 4,952,213 A | 8/1990 | Bowman et al. | |
| 5,082,003 A | 1/1992 | Lamb et al. | |
| 5,445,642 A | 8/1995 | McNulty et al. | |
| 5,484,446 A * | 1/1996 | Burke et al. | 606/87 |
| 5,571,110 A | 11/1996 | Matsen, III et al. | |
| 5,681,316 A | 10/1997 | DeOrio et al. | |
| 5,682,886 A | 11/1997 | Delp et al. | |
| 5,688,279 A | 11/1997 | McNulty et al. | |
| 5,997,539 A * | 12/1999 | Errico et al. | 606/278 |
| 6,021,343 A * | 2/2000 | Foley et al. | 600/429 |
| 6,033,410 A | 3/2000 | McLean et al. | |

(Continued)

FOREIGN PATENT DOCUMENTS

EP 104 732 4/1984

(Continued)

*Primary Examiner*—Eduardo C Robert
*Assistant Examiner*—Tara R Carter
(74) *Attorney, Agent, or Firm*—Ogilvy Renault LLP

(57) ABSTRACT

A positioning block (10) for use in total knee replacement surgery, permitting five degrees-of-freedom movement relative to a bone element (39) to which it is fixed. The positioning block (10) comprises a rotational mounting element (14) that is removably engaged to the bone element such that the mounting element (14) is selectively rotatable relative to the bone element, about three substantially perpendicular axes of rotation. A guide body portion (12) is engaged with the mounting element (14) such that it is translatable relative thereto along a proximal-distal axis (43) and an anterior-posterior axis (47), while being rotationally fixed relative to the mounting element (14) such that the guide body portion (12) and the mounting element (14) rotate together relative to the bone element (39).

9 Claims, 17 Drawing Sheets

U.S. PATENT DOCUMENTS

| | | | |
|---|---|---|---|
| 6,056,756 | A | 5/2000 | Eng et al. |
| 6,139,493 | A | 10/2000 | Keros et al. |
| 6,478,799 | B1 | 11/2002 | Williamson |
| 2001/0018589 | A1 | 8/2001 | Muller |
| 2002/0068942 | A1* | 6/2002 | Neubauer et al. ............. 606/88 |
| 2002/0095083 | A1 | 7/2002 | Cinquin et al. |
| 2002/0133161 | A1* | 9/2002 | Axelson et al. ............... 606/88 |

FOREIGN PATENT DOCUMENTS

| | | |
|---|---|---|
| EP | 380 451 | 1/1990 |
| FR | 2 690 067 | 10/1993 |
| WO | WO 02/36031 | 5/2002 |

\* cited by examiner

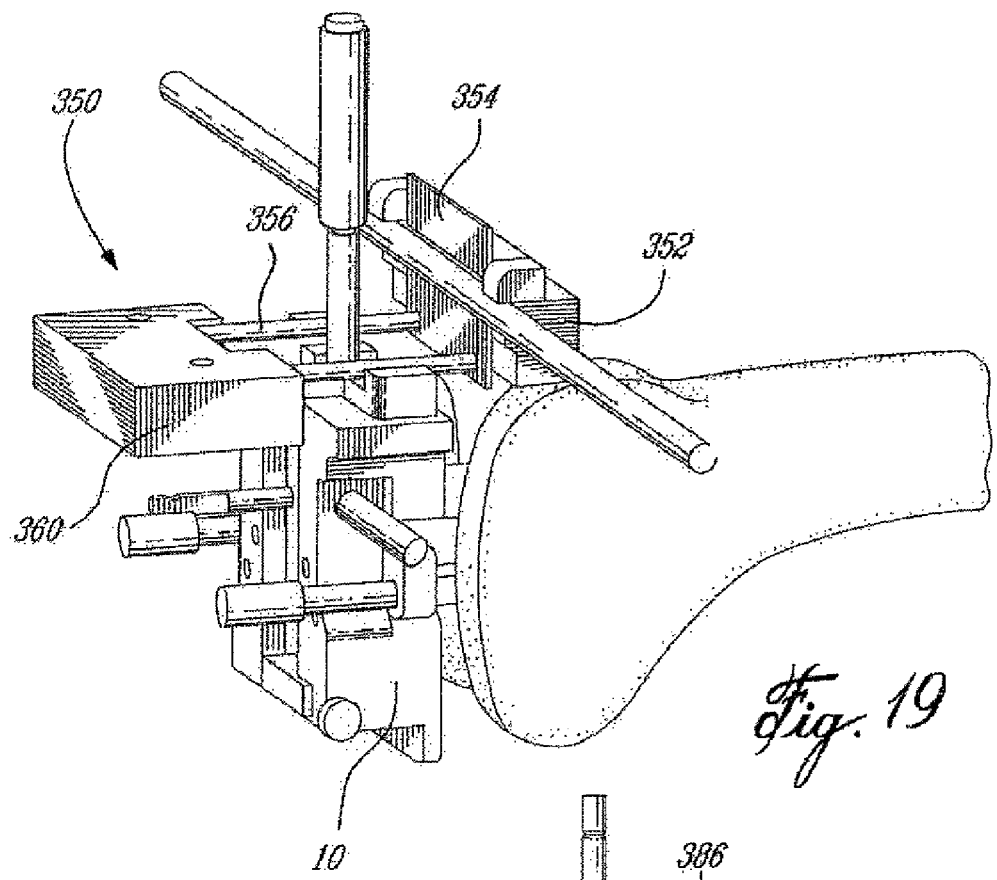
Fig. 19
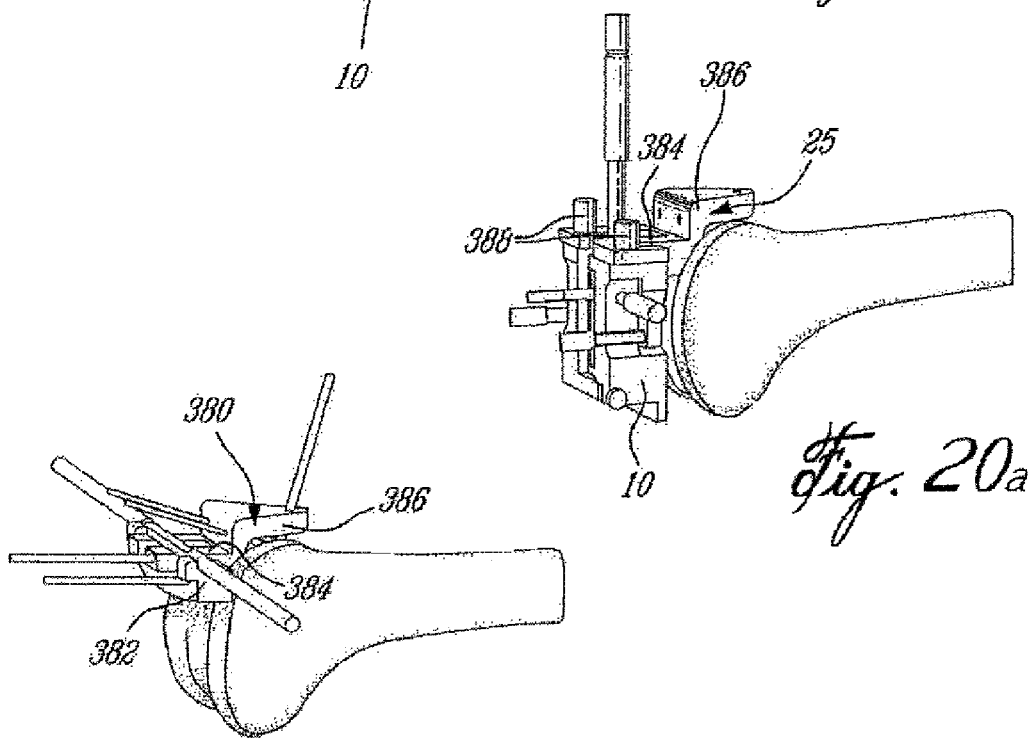
Fig. 20a
Fig. 20b

SURGICAL UNIVERSAL POSITIONING BLOCK AND TOOL GUIDE

CROSS-REFERENCE TO RELATED APPLICATIONS

This a divisional application of U.S. patent application Ser. No. 11/062,737 filed Feb. 23, 2005, now U.S. Pat. No. 7,736,368 which is a continuation of International Patent Application Serial No. PCT/CA03/01307 filed Aug. 25, 2003, which claims priority on: U.S. Provisional Application No. 60/405,353, filed on Aug. 23, 2002; U.S. Provisional Application No. 60/405,326, filed on Aug. 23, 2002; and U.S. application Ser. No. 10/357,493, filed on Feb. 4, 2003; the entire contents of each of these patent applications is incorporated herein by reference.

FIELD OF THE INVENTION

The present invention relates generally to a surgical tool for use in knee surgery. More particularly, the present invention is directed to a multiple degree-of-freedom positioning reference block and a surgical tool guide, for use in computer assisted surgery (CAS) total knee replacement.

BACKGROUND OF THE INVENTION

Accuracy of cuts and drilled holes is important in knee arthroplasty, wherein installation of the implants such that the kinematics of the natural knee are duplicated as much as possible, is important to the success of the total knee replacement. To achieve this, the use of CAS systems for orthopedic operations in general, and for total knee replacement surgery in particular, is becoming increasingly more commonplace with advancements in CAS equipment that ensure improved accuracy, fail safe operation and increasing ease of use.

Known camera based CAS system employ passive and active trackable elements affixed to objects, such as surgical tools and patient bone references, in order to permit the determination of position and orientation of the objects in three-dimensional space. Preoperatively taken images or computer generated models created from preoperative patient scans, are used to provide accurate patient anatomical information to which the real-time position of the same anatomical elements can be registered or calibrated, thereby permitting subsequent tracking of the anatomical elements and display of these elements relative to the surgical tools used during the surgery.

Total knee replacement surgery requires several precise cuts to be made in the femur and tibia, such that the implant fits correctly and best replicates the geometry of a natural healthy knee. To perform these steps, in both conventional and CAS total knee replacement, it is well know to use a guide block which provides a drill and/or cutting guide to assist the surgeon to perform the steps required to prepare the femur and tibia for receiving the implant.

In order to best understand the improvement the present invention provides over such guide blocks of the prior art, it is necessary to understand the steps performed during a typical total knee replacement surgery to prepare the bones for receiving the implants.

The typical method steps used to prepare the femur for a knee replacement implant, outlined below as an example, generally include: fastening a guide block on the femur, generally located by an intramedullary pin or screw inserted into the distal end of the femur and locating the guide block in the desired position; aligning a distal cutting guide, whether being integral with the guide block or a separate element fastenable thereto, in a predetermined location relative to the guide block reference position and inserting locating pins through the distal cutting guide and into the femoral condyles to fasten the cutting guide in place on the anterior surface of the distal end of the femur; removing the distally mounted guide block, leaving the distal cutting guide pinned to the anterior surface of the femur; making the distal cut to resect the predetermined amount of bone from the distal end of the condyles; positioning the guide block freely on the newly cut distal surface of the femur and ensuring that the resection level for the anterior cut, the anterior-posterior adjustment for implant sizing, the rotational alignment and medial-lateral position of the positioning block are all correct before fixing the guide block in place with pins; removing the positioning guide block, putting the peg hole drill guide block onto the pins, and drilling the implant peg holes; and using these peg holes to install an anterior-posterior cutting block which is then used to perform the anterior cut, and subsequently to install an appropriately sized chamfer cutting block which is then used to make the anterior-posterior chamfer and notch cuts.

The steps required to prepare the tibia are less involved. Generally, they include: aligning the mechanical axis of the tibia; obtaining proper rotational alignment of the guide block, and fastening it in place to the anterior surface of the proximal end of the tibia; adjusting the guide block to ensure the desired posterior slope and level of tibial resection are provided; inserting location pins using the guide block; removing the guide block and replacing it with a tibial resection cutting guide that is retained in place with the location pins; and resecting the chosen amount of tibial bone.

The above surgical procedures remain generally similar whether traditional or computer assisted surgery is being performed. As such, the use of a cutting/drill positioning block having a position identifying member fastened thereto and trackable by a camera based CAS system, for example, is known for use in total knee replacement surgery. However, while such tracked femoral positioning guide blocks provide significant advantages over traditional non-CAS instruments, there nevertheless remains room for improvements to the current guide blocks used in total knee replacement surgery, whether being a guide block for use with an image guided CAS system or traditional non-computer aided surgery, in order to further simplify surgical procedures and to enhance accuracy.

As discussed above, known total knee replacement procedures include creating a distal on the femur in order to resect enough bone to permit the installation of the femoral implant. In conventional, or non computer assisted, total knee replacement surgery a distal cutting block is positioned and aligned by the surgeon and pinned in place on the anterior surface of the femur such that the cutting slot is aligned in the correct location for the distal cut. In CAS total knee replacement, it is also known to use a distal pin drill guide to accurately create the pin holes into which locating pins are inserted and employed to fix the distal cutting guide, either integrally formed with the distal pin drill guide or being a separate element, in the correct location to make the distal cut in the femur. Generally, the distal drill/cutting guide member comprises part of an assembly including an anterior guiding platform, that is fixed relative to the femur and on which the drill/cutting guide is displaceable by a selected, measurable amount to locate the drill/cutting guide in a desired position relative to the anterior guiding platform and therefore relative to the distal end of the femur. A tracked guide block is often intramedullarly fastened to the femur, and the anterior guiding platform can then be engaged thereto. Depending on the type of implant being used, and once aligned with the most distal femoral condyle, the drill/cutting guide can then be proximally displaced on the fixed anterior guiding platform by a selected amount corresponding to the amount of bone to be resected.

A captive spring loaded plunger, located within the distal drill/cutting guide, is known to comprise a pointed pawl portion, which engages a series of notches located on the anterior guiding platform to fix the distal drill/cutting guide in place thereon. Demarcations on the guiding platform indicate resection distance, and the spring loaded plunger can be depressed to release the pawl from the notches and consequently permit movement of the drill/cutting guide along the guiding platform. As the notches are formed such that the distance between each notch accurately corresponds to a single unit of distance, for example 2 mm, a precise resection distance can be achieved by depressing the spring-loaded plunger and sliding the guide on the fixed platform the required number of notches. Demarcations on the platform provide a visual indication of the position of the guide block position.

This spring loaded mechanism is effective to permit displacement of the drill/cutting guide when required and to fix the guide in place when the guide is correctly aligned by releasing the outwardly biased plunger. However, such currently known mechanisms generally use a blind hole which receives a helical spring and the plunger therein, the plunger being permanently retained within the guide. This often causes sterilization problems, as cleaning the spring and inside bore of the mechanism becomes difficult because the captive plunger can not be removed. As a result, bacteria can build up inside the bore, and can not be easily cleaned out and sterilized. This becomes a major problem as cleanliness is paramount in surgical environments.

As CAS systems permit improved visualization of the positioning block relative to the bone elements of the femur and projected reference block axes superimposed relative to those of the bone element, fewer fixed anatomical reference surfaces need to be used in conjunction with tracked CAS positioning reference blocks. However, to best permit temporary fixation block in a determined position, the reference block requires controllable adjustment of several degrees of freedom. While certain flexibility is provided by total knee replacement positioning guide blocks of the prior art, there nevertheless remains a need for a more universal positioning block permitting additional controllable flexibility of movement, and being adapted for use with a CAS system.

SUMMARY OF THE INVENTION

Accordingly, it is an object of the present invention to provide a positioning block for total knee replacement surgery having improved mobility.

It is another object of the present invention to provide a positioning block permitting proximal-distal adjustment when engaged with the distal end of the femur.

It is another object of the present invention to provide an improved distal drill and/or cutting guide for use in total knee replacement surgery, being adaptable to different implant types and capable of simplified location of the distal cut reference.

It is another object of the present invention to provide a surgical tool guide having a biased pawl mechanism that can be easily dismantled for cleaning.

There is therefore provided, in accordance with the present invention, a method of installing a surgical positioning block on a bone element, the positioning block having a reference surface and being operatively engageable with a cutting tool, the method comprising: fastening the positioning block to the bone element; determining a desired position of the reference surface of the positioning block relative to the bone element; adjusting at least one of the position and orientation of the positioning block, until the reference surface is in the desired position; and using the reference surface in the desired position as a reference for locating the cutting tool in a predetermined location on the bone element, such that a cut can be made in the bone element at the predetermined location.

In accordance with the present invention there is also provided a positioning block for use in total knee replacement surgery, permitting five degrees-of-freedom movement relative to a bone element to which it is fixed, the positioning block comprising: a rotational mounting element being removably engageable to the bone element such that the mounting element is selectively rotatable relative to the bone element, about three substantially perpendicular axes of rotation; and a positioning body portion being engaged with the mounting element such that it is translatable relative thereto along a proximal-distal axis and an anterior-posterior axis, while being rotationally fixed relative to the mounting element such that the positioning body portion and the mounting element rotate together relative to the bone element.

There is also provided, in accordance with the present invention, a computer assisted total knee replacement surgery system comprising: a positioning block being fastenable to a bone element; means for determining the position and orientation of the positioning block relative to the bone element; the positioning block having a reference surface and being operatively engageable with a cutting tool; means for identifying a desired position of the positioning block relative to the bone element, such that the reference surface is located in a position relative to the bone element whereby the cutting tool, disposed in a known position relative to the reference surface, is located in a selected position relative to the bone element, such that a cut can be made in the bone element at the selected position; and a display capable of indicating when the desired position of the positioning block is reached.

There is further provided, in accordance with the present invention, a surgical positioning block permitting at least two independently adjustable degrees-of-freedom relative to a bone element to which it is engaged, the positioning block comprising: a positioning body being operatively engageable with a cutting tool and including a reference surface, the positioning body being engageable to the bone element such that independent movement in at least two degrees-of-freedom relative thereto is selectively possible for adjustment purposes; and the positioning body comprising at least two independent adjustment mechanisms, each adjustment mechanism being adjustable in isolation for respectively displacing the positioning block in one of said at least two degrees-of-freedom, such that the reference surface can be located in a desired position and used as a reference to position the cutting tool in a predetermined location for making a cut in the bone element.

There is also provided, in accordance with the present invention, a surgical instrument comprising: a first member and a second member being slidingly displaceable relative to one another, the first member having one of a rack and a pawl of a rack and pawl mechanism, and the second member having the other of the rack and the pawl; an elastically deflectable blade spring, the blade spring biasing one of the rack and the pawl such that they are normally engaged together; whereby the first and second members are slidingly displaceable relative to each other when the rack and pawl are disengaged, and fixed relative to each other when the rack and pawl are in engagement; and the first and second members having substantially seamless surfaces that are at least one of substantially exposed and exposable, such that the surfaces can easily be pressure cleaned and autoclaved to remove biological matter therefrom.

There is also provided, in accordance with the present invention, a surgical tool guide for preparing the femoral portion of a knee in a total knee replacement surgery, comprising: a guide block having at least one of a drill guide hole and a distal cutting guide slot, and comprising an elastically deflectable blade spring; an anteriorly mounted platform, comprising a toothed rack and providing support for the guide block such that proximal-distal sliding displacement of the guide block thereon is permitted; the platform being adapted for mounting to a femoral reference positioning guide member distally fastened to the femur; the guide block and the platform having substantially seamless surfaces that are at least one of substantially exposed or exposable, such that the surfaces can easily be pressure cleaned and autoclaved to remove biological matter therefrom; and a pawl being normally biased by the blade spring such that it is in engagement with the toothed rack on the platform; whereby the guide block is displaceable relative to the platform when the biased pawl is disengaged from the toothed rack and fixed relative thereto when the pawl is engaged with the toothed rack.

BRIEF DESCRIPTION OF THE DRAWINGS

These and other features, aspects and advantages of the present invention will become better understood with regard to the following description and accompanying drawings wherein:

FIG. 11b is a side elevation view of the universal positioning block of FIG. 7, alternately mounted on the polyaxial screw of FIG. 11a;

FIG. 15 is an exploded perspective view of the distal drill/cutting guide block of FIG. 5a;

FIG. 17b is a side elevation view of the plunger of FIG. 17a;

FIG. 17c is a front elevation view of the tool guide of FIG. 17a;

FIG. 19 is a perspective view of a universal distal cutting guide adaptor mounted on the universal positioning block and being used to locate a standard distal cutting guide block;

FIG. 20a is a perspective view of a universal anterior cutting guide adaptor mounted on the universal positioning block; and FIG. 20b is a perspective view of the universal anterior cutting guide adapter of FIG. 20a pined in place on the femur and being used to locate a standard anterior cutting guide block.

DETAILED DESCRIPTION OF THE PREFERRED EMBODIMENT

Throughout this application, the preferred embodiment of the present invention will be referred to as a universal positioning block or simply positioning block, and is preferably for use in total knee replacement surgery and is adapted to accurately position and align a cutting tool. The universal positioning block comprises a guide body or cutting tool guide element that is operatively engageable with a cutting tool, whether directly by providing a cutting guide surface on the cutting tool guide element itself or by being engageable with a separate cutting guide block which is used to guide the cutting tool. It is to be understood that such a cutting tool as defined herein includes all instruments which can remove bone from a bone element, such as drills and saws for example, and that such a cutting tool guide element or surface thereon is similarly adapted for guiding any instrument which can remove bone from a bone element such as a drill bit or a saw blade.

Preferably, the universal positioning block is trackable by a computer assisted surgical (CAS) system which provides means for determining the position, orientation and movement of the universal positioning block in three dimensional space, and permits the positioning block to be visualized relative to the patient anatomy. The CAS system further provides means for determining a desired position of the universal positioning block relative to a bone element, whether from a real patient, a cadaver or a model. The CAS system further provides means for indicating where to fasten the universal positioning block on such a bone element such that it can be adjusted into the desired position. However, the present universal positioning block can equivalently be used in conventional, or non-computer assisted, surgical applications. Additionally, the present universal positioning block can be used with both CT-based and CT-less CAS systems. The CAS system can, in other words, use either computer generated anatomical models created from pre-operatively taken scans, such as CT scans, or use intra-operatively generated bone surface models created by digitizing a plurality of points and anatomic landmarks on the surface of the bone element, to relate the position of the universal positioning block to the bone elements of the patient.

Figure 1:
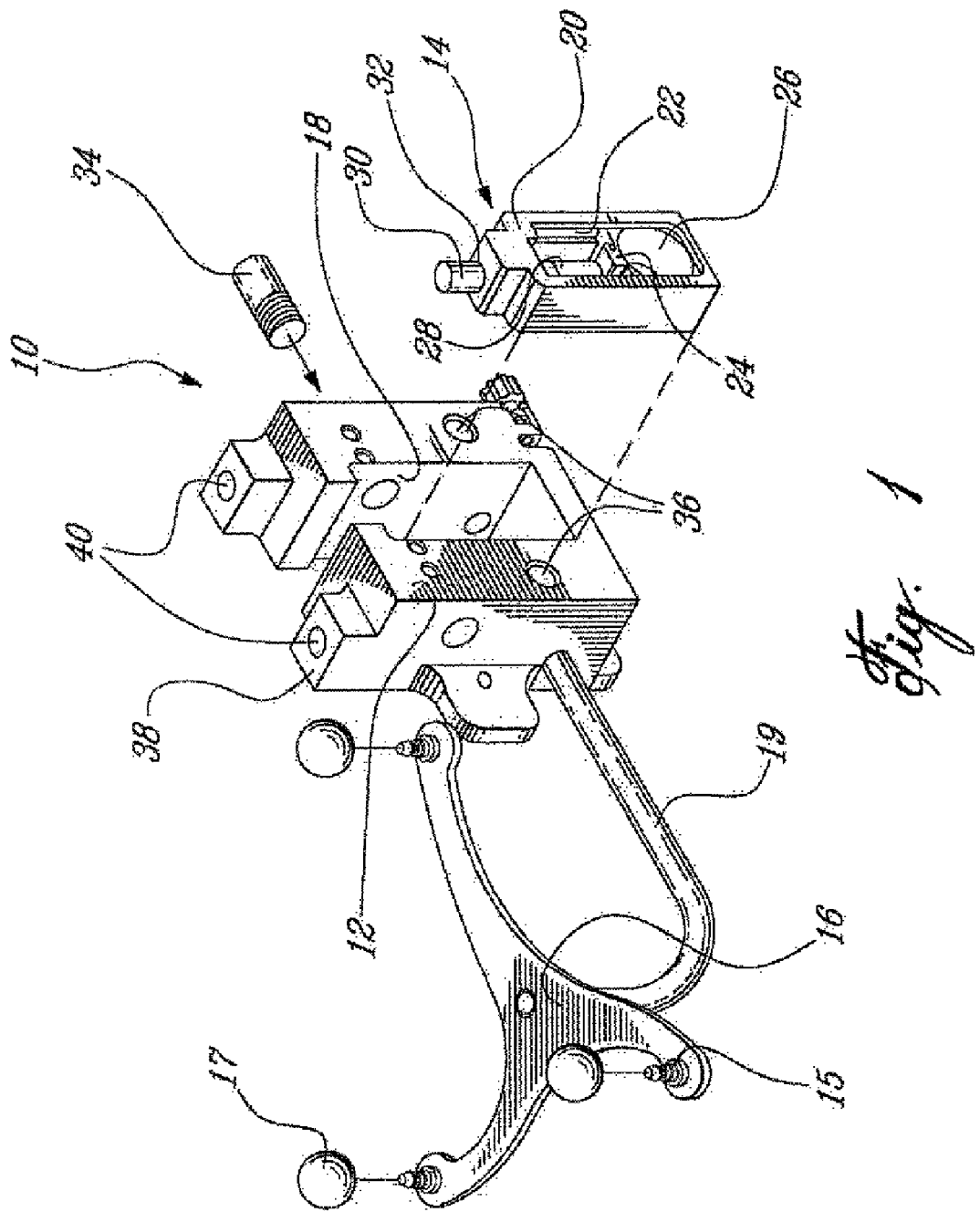
FIG. 1 is an exploded perspective view of a trackable CAS universal positioning reference block according to the present invention.

Referring to FIG. 1, the universal positioning block assembly 10 comprises generally a cutting tool guide element or guide body member 12, a mounting member 14 and a tracker member 16. The tracker member 16 comprises at least three detectable elements 17, engaged to the trackable member via mounting posts 15. The detectable elements 17 are preferably spherical passive markers locatable by a camera-based, optical tracking GAS system. However, it is to be understood that active optical markers can equivalently be used as the detectable elements, and that CAS systems using electromagnetically and acoustically detectable elements can also similarly be employed. The main guide body 12 comprises a large central aperture 18 for receiving the mounting member 14 therein. The guide body 12 comprises cutting guide surfaces, such as the two drill guide holes 36, which extend through the guide body 12. The guide body 12 also includes means for engagement to a cutting guide, comprising, for example, a pair of mounting points 38 having peg holes 40 are disposed on the top of the guide body, permitting engagement with another drill/cutting guide block for example. The mounting member 14 comprises a translation mechanism including a fastener receiving mount element 24, which slides within the central guide slot 22 disposed within the mounting member body 20. The fastener mount element 24 comprises a semi-spherically shaped bowl 26 which has a through hole at the bottom thereof. The fastener mount element 24 is displaced relative to the mounting member body 20 by an endless screw 28, engaged to the fastener mount element and extending through an inside-threaded hole 32 in the mounting member body 20. The translation screw 28 is actuated by a screw head 30, such that rotation of the screw head 30 causes the fastener mount element 24 to be translated within the central guide slot 22. The translation, or elevation, screw 28 thereby enables the entire positioning block to be raised or lowered along an anterior-posterior axis when engaged to a distal end of a femur. The entire mounting member 14 additionally slides within the central aperture 18 of the guide body 12, generally permitting the guide body to be displaced along a proximal-distal axis when the positioning block is engaged to a distal end of a femur. A friction locking screw 34 extends through the side of the guide body and engages the mounting member 14, such that it can be retained in a selected position relative to the guide body 12.

Figure 2:
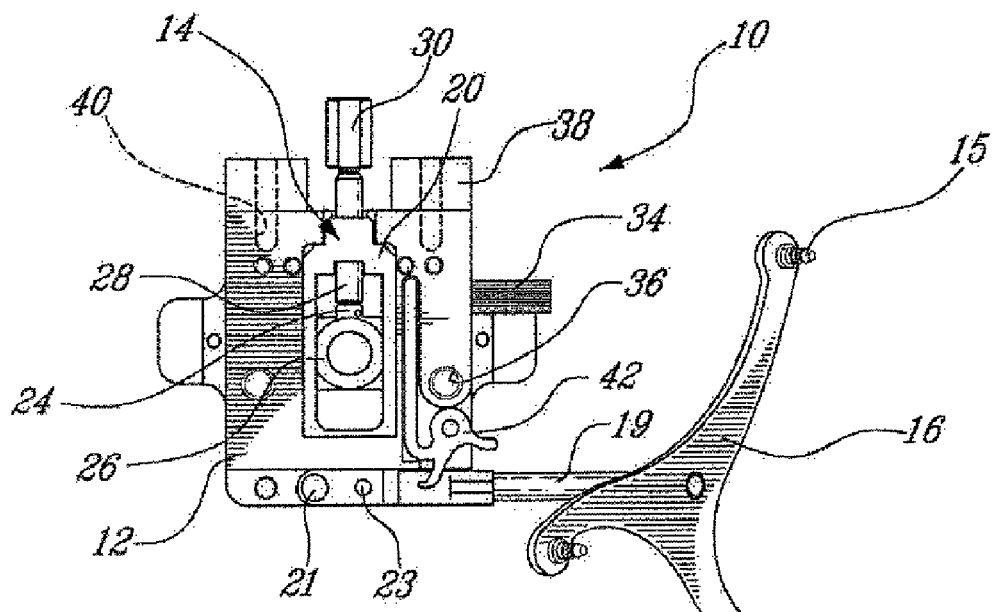
FIG. 2 is a front elevation view of the universal positioning reference block of FIG. 1.

The universal positioning block 10 is shown assembled in FIG. 2, however with the trackable member 16 alternately mounted, via the tracker stem 19 pivotable about pivot 21, on the opposite side of the guide body 12. A locking screw 23 is preferably used to fix the trackable member 16 in place on the selected side of the universal positioning block 10. The trackable member can be fixed in position on the guide body, or removably engaged to either side of the guide body of the positioning block, such that the best visual contact between the detectable elements and the cameras of the CAS system is ensured. For example, if the trackable member is removably engageable, it can be switched sides of the guide body depending on which knee is being operated on, thereby reducing the need to displace the cameras or other equipment of the image guided surgery system. A removably lockable quick release can alternately be used in place of the fixed pivot 21 and the locking screw fastener 23, to retain the stem 19 in place within the guide body 12, such that no movement of the trackable member 16 relative to the guide body is permitted, while nevertheless permitting removal to the stem from the guide body when required.

Figure 5B:
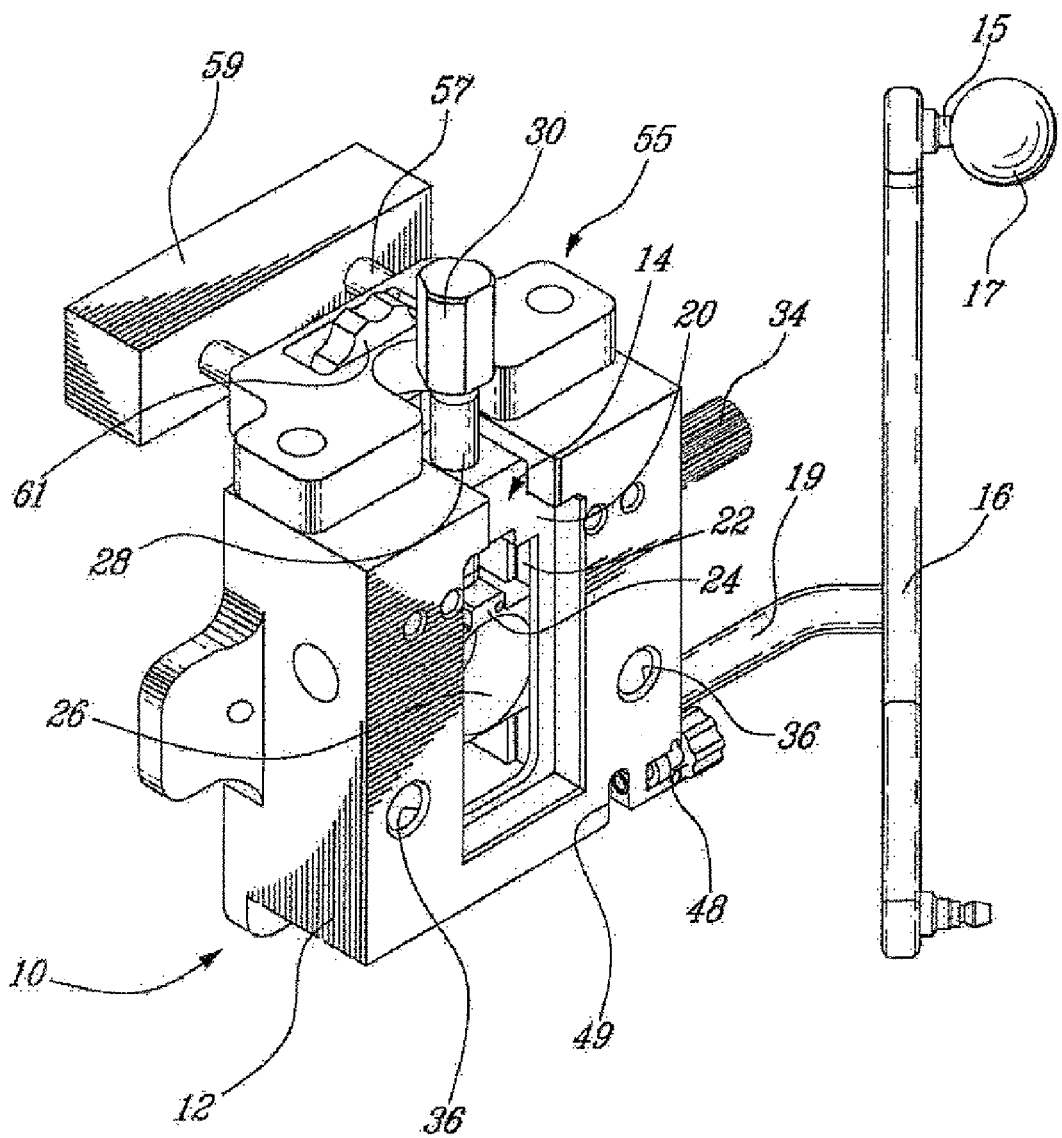
FIG. 5b is a perspective view of the CAS universal positioning block of the present invention assembled with an alternate cutting guide block.
Figure 6:
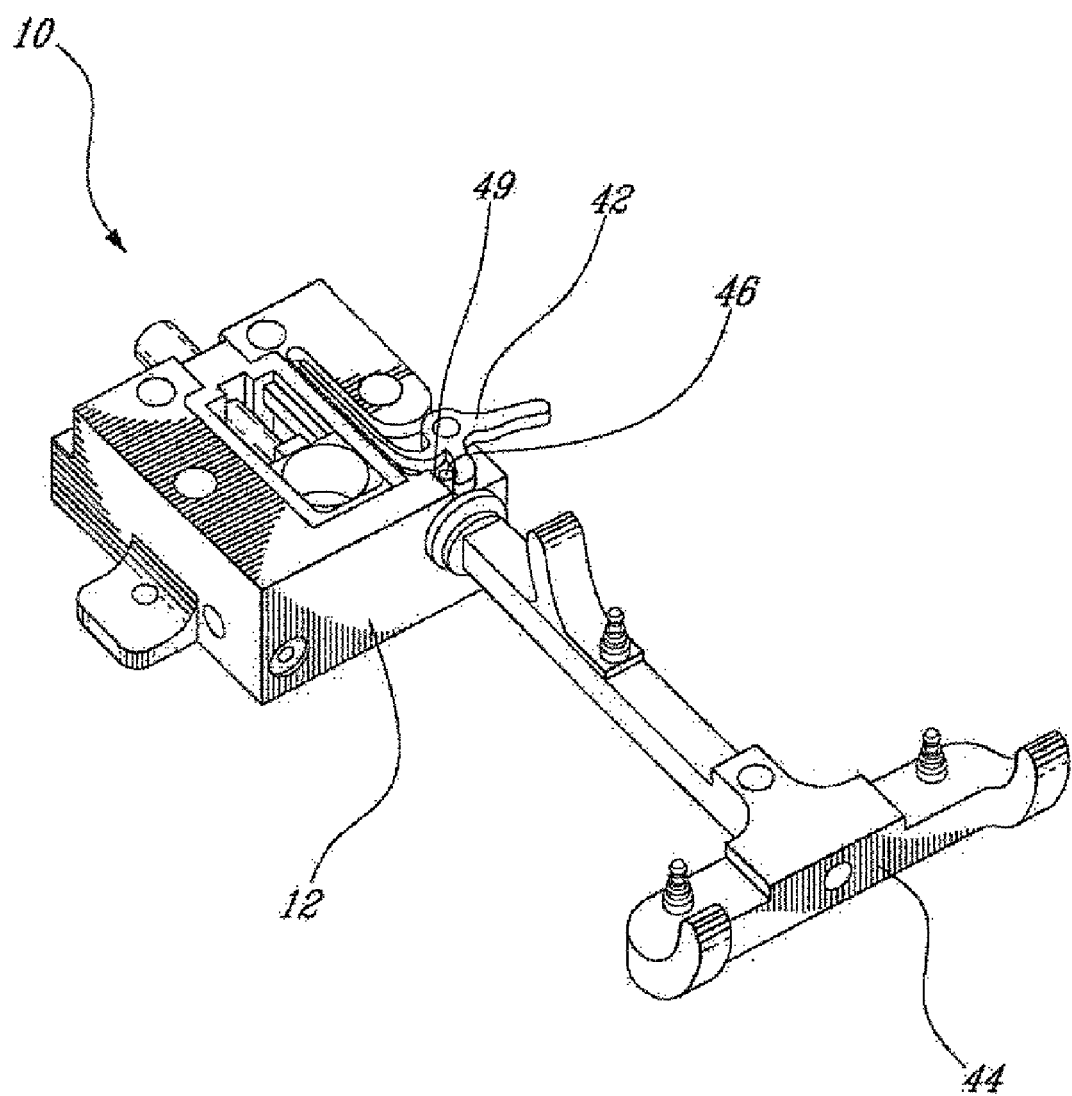
FIG. 6 is a perspective view of the universal positioning block of FIG. 2 with a calibration instrument engaged thereto.

As best seen in FIG. 6, the guide body 12 also preferably comprises a socket disposed in an underside edge and a releasable retention member 42. The socket is adapted to receive an automatic calibration instrument 44, comprising another set of detectable elements thereon. The calibration instrument 44, which is permanently calibrated, permits calibration of the tracked positioning block, such that by securely engaging it with the tracked positioning block the position and orientation in space of the detectable elements 17 of the trackable member 16 are determined relative to similar detectable elements of the removable calibration instrument 44, which are themselves in a known position in space. The position and orientation of the positioning block 10 can therefore be calibrated, such that the image guided surgical system can accurately track it in three dimensional space. The automatic calibration instrument 44 preferably snaps into engagement with the guide body 12 of the positioning guide block. An alignment pin 46 located on the calibration instrument fits into a corresponding notch 49 in the guide body, to ensure that the calibration instrument 44 is correctly oriented relative to the positioning guide block. The biased retention member 42 on the positioning block engages the calibration instrument 44 via the alignment pin 46, thereby securely retaining the calibration instrument within the mating socket of the guide block while the calibration procedure is performed. Once completed, the lever portion of the releasable retention member 42 is actuated, thereby releasing the portion of the retention member in contact with the alignment pin 46 of the calibration instrument and permitting the calibration instrument 44 to be disconnected from the positioning block. Alternate retention members can equivalently be used. For example, as seen in FIG. 5b, a friction screw retention member 48 is similarly used to selectively retain the calibration instrument connected with the positioning block. Additionally, no retention member may be required if the calibration instrument can be engaged with the positioning block in such a way that it is precisely located and cannot be easily displaced while the calibration process is being performed.

Figures 13, 14:
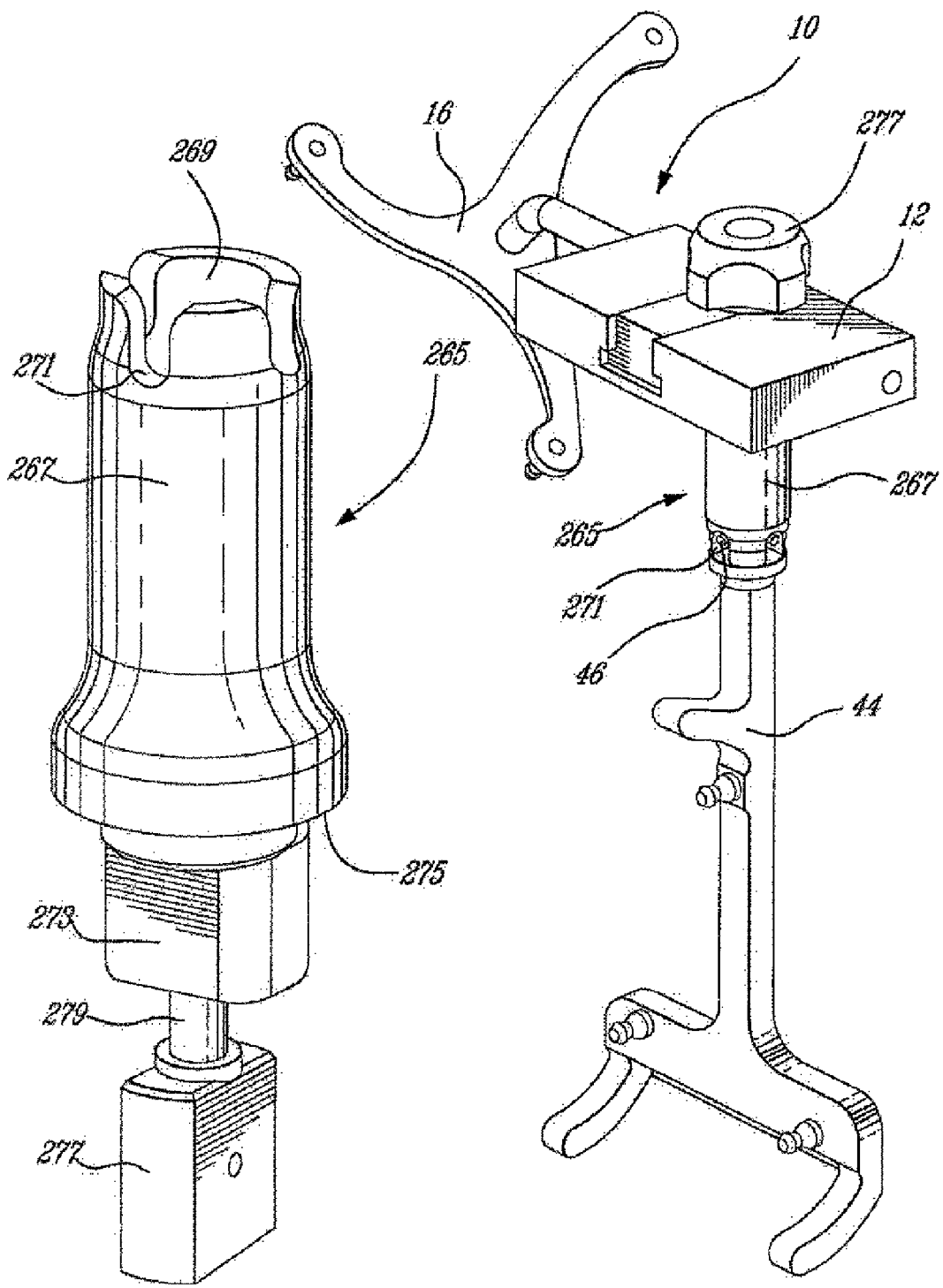
FIG. 13 is a perspective view of an automatic calibrator adaptor for use with the universal positioning block of the present invention.
FIG. 14 is a perspective view of the automatic calibrator adaptor of FIG. 13 assembled with the universal positioning block and the calibration instrument of FIG. 6.

Referring to FIGS. 13 and 14, which depict an alternate method of temporarily fastening the calibration instrument 44 to the universal positioning block 10 using a separate automatic calibrator adaptor 265. Particularly, the automatic calibrator adaptor 265 comprises a generally cylindrical body 267 within which the calibration instrument 44 can be inserted via opening 269 at a first end thereof. Several grooves 271 are provided to receive the alignment pin 46 of the calibration instrument 44 therein. Integrally formed at a second of the body 267 is a positing block engaging member 273, sized to fit within the central slot 22,122 disposed within the mounting member body 20,120 of the positioning block 10, 110. The positioning block engaging member 273 of the automatic calibrator adaptor 265 can thus be inserted with the central slot 22,122 and can be clamped therein by tightening the screw 28,128 to displace the fastening receiving mount element 24,124 until it clamps the positioning block engaging member 273 of the automatic calibrator adaptor 265 between the fastening receiving mount element 24,124 and the base of the mounting member body 20,120. The flange 275 of the automatic calibrator adaptor 265 preferably abuts a surface of the guide body 12,112. The automatic calibrator adaptor 265 further comprises a screw head 277 which rotates screw body 279 within the automatic calibrator adaptor 265, and is used to fasten the calibration instrument 44 within the automatic calibrator adaptor 265 by threaded mating engagement with an internally threaded socket in the calibration instrument 44. The automatic calibrator adaptor 265 therefore permits the universal positioning block 10,110 and the calibration instrument 44 together in a locked position, such that the universal positioning block 10,110 can be easily calibration when the three elements are fastened together and shown to the cameras of the computer assisted surgery system. As the calibration instrument is always calibrated and hence in a known position, the relative position of the detectable elements 17 of the universal positioning block 10,110 to those of the calibration instrument 44 can be computed by the CAS system.

Figure 3:
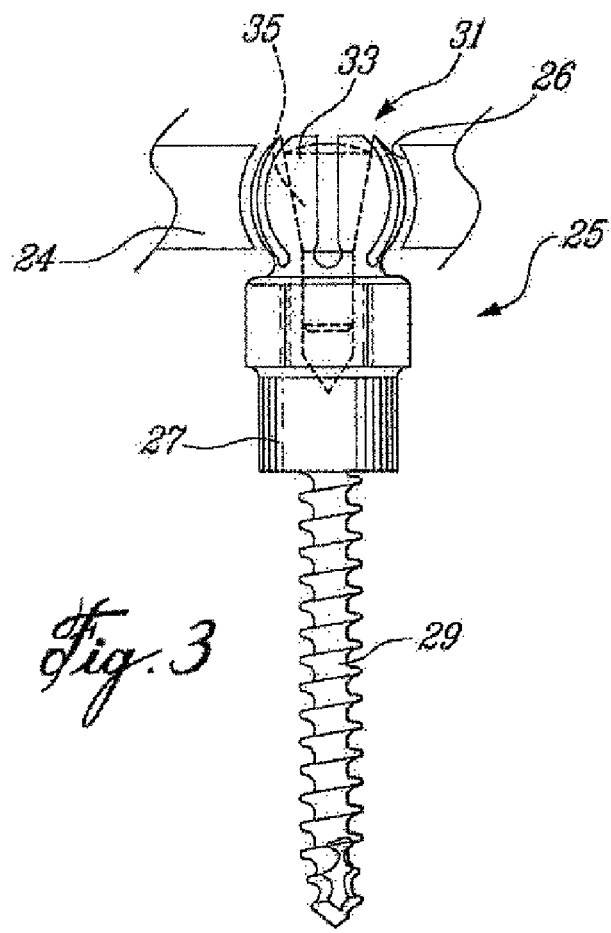
FIG. 3 is a side elevation view of a polyaxial mounting screw element used to fasten the universal positioning reference block of FIG. 2 to a bone element.

A polyaxial mounting screw 25, as best seen in FIG. 3, is used to mount the universal positioning block 10 to the bone. The polyaxial screw 25 comprises generally a main screw body 29 having threads on the outside, a shoulder portion 27, and a spherical screw head 31 having a plurality of integrally formed individual petal elements 33. A central conical screw 35 is inserted through the center of the screw head, and when engaged therein, forces the petal elements 33 outwards, thereby causing them to press against the semi-spherical surface 26 of the fastener mount element 24. This consequently immobilizes the fastener mount element 24 in position on the spherical polyaxial screw head 31, fixing it in position thereon. The petal elements 33 are slightly elastically deflectable and the polyaxial screw head 31 is sized such that the petal elements are forced slightly radially inward when the fastener mounting element is pressed down overtop, and engaged to the screw head. This ensure that once snapped in place, the fastener mount element 24, and subsequently the entire positioning block assembly, can freely rotate about the polyaxial screw head in three rotational degrees of freedom. Once the positioning block is aligned in the desired position, the conical screw 35 at the center of the polyaxial screw head 31 can be tightened, thereby rotationally fixing the guide block assembly in place on the polyaxial mounting screw 25. When the term polyaxial screw is used herein, it is to be understood that it comprises preferably a screw having a substantially spherical head. The spherical head permits a ball and socket type joint to be created, when an element with a receiving socket is engaged with the ball head of the polyaxial screw. The spherical head preferably, but not necessarily, includes the individual petal elements that are displaceable by the central conical screw in order to provide a locking mechanism. Other mechanism to lock the member with the receiving socket in a selected position on the head of the screw are equivalently possible.

Figure 4A:
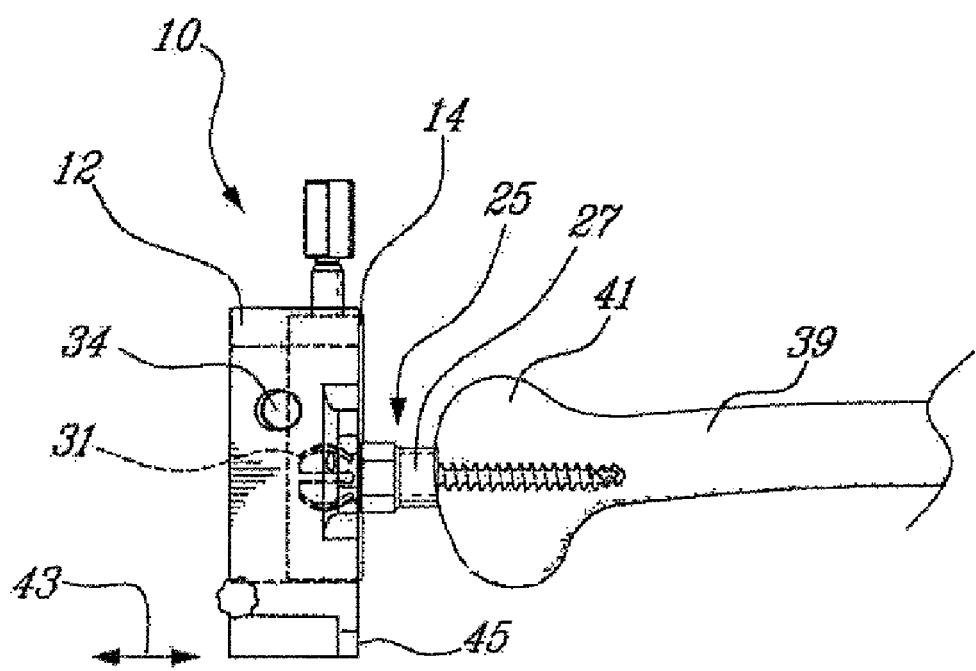
FIG. 4a is a side elevation view of the universal positioning reference block of the present invention mounted to a femur.
Figure 4B:
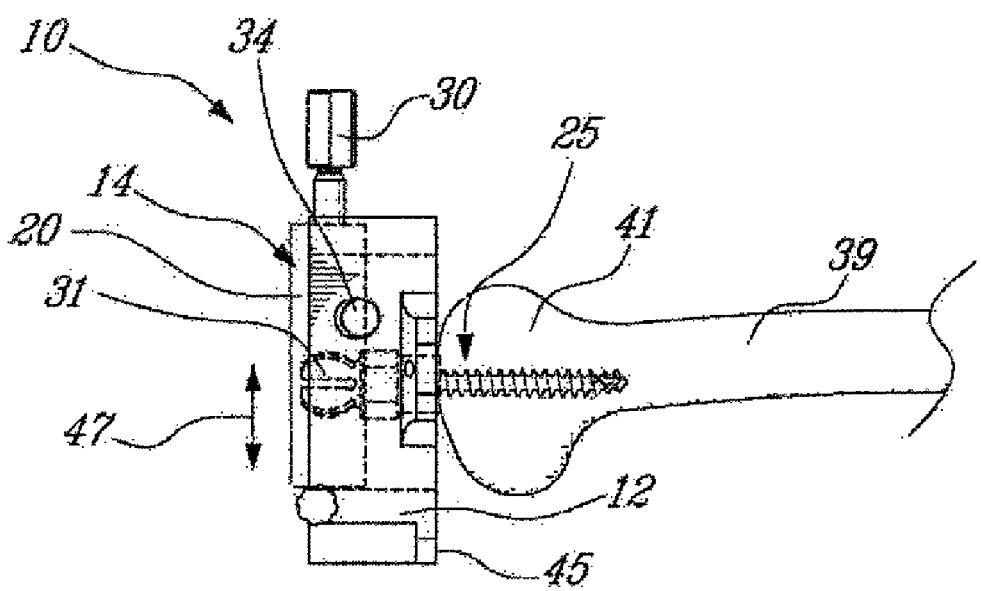
FIG. 4b is a side elevation view of the universal positioning reference block of the present invention mounted to a femur and the positioning body proximally displaced such that it abuts the femur.
Figure 12:
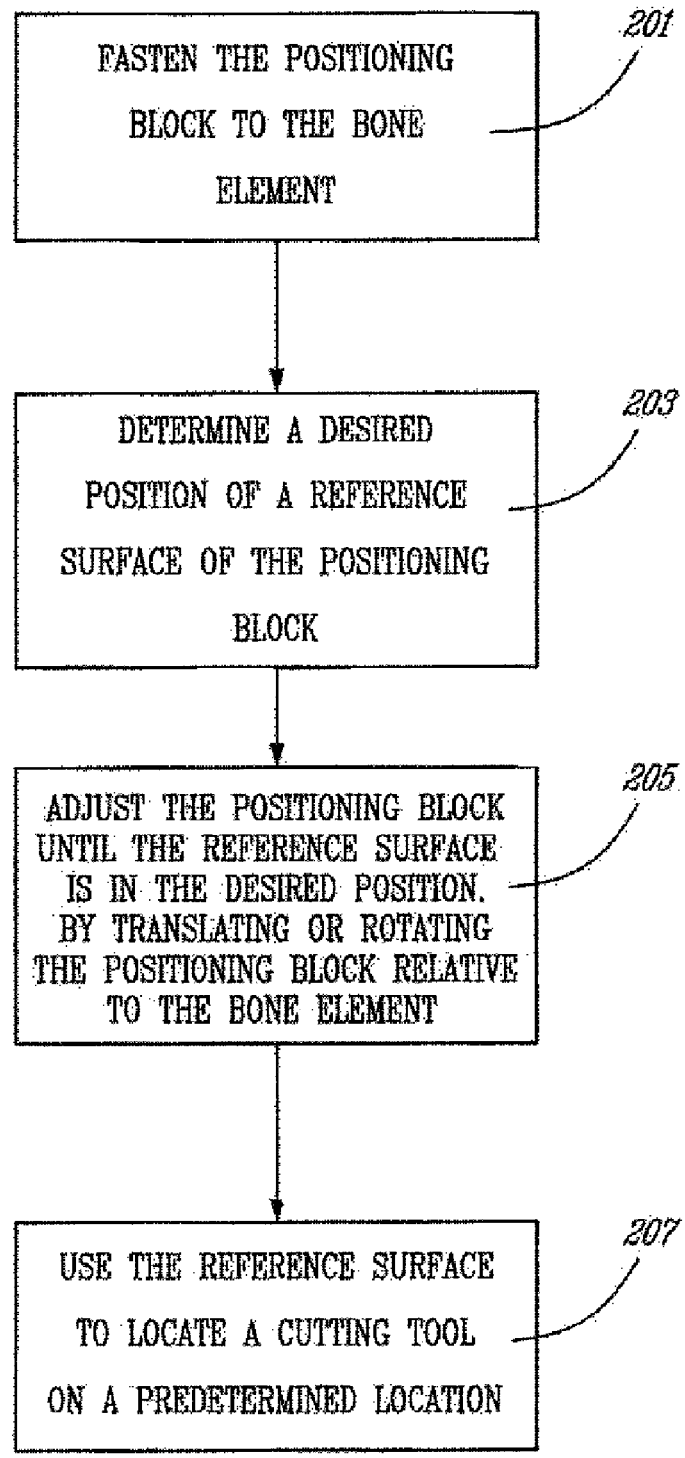
FIG. 12 is a schematic flow chart of the method used to install the universal positioning block of the present invention to a bone element.

Referring now to FIGS. 4a and 4b, showing the universal positioning block assembly 10 mounted to the distal end of a femur 39 by the polyaxial screw 25, and to FIG. 12 showing method steps involved with installing the positioning block on a bone element. The degree of mobility of the universal positioning block 10 permits significant simplification of the surgical procedures employed in certain surgeries, such as total knee replacement surgery. Generally, the first step 201 comprises fastening the positioning block 10 to the bone element. As shown in FIG. 4a, this is preferably done using the polyaxial screw 25, which is first aligned with the entrance point of the mechanical axis at the distal end of the femur and introduced therein until its shoulder 27 touches the bone. The fastener mount element 24 of the universal positioning block 10, as best seen in FIG. 1 and FIG. 2, is snapped onto the head 31 of the polyaxial screw.

The step 203 of determining a desired position of the positioning block 10, or a portion thereof such as a reference surface 45 on the guide body 12, is done by either by the CAS system itself, by the surgeon using the CAS system as a guide or independently by the surgeon, in order to determine what final position the positioning block 10 should be moved into in such that a drilled hole or a sawn cut can be made in the bone element at a predetermined location that is required for the installation of an implant. Step 205 comprises adjusting the position and orientation of the positioning block 10 until it, or a portion thereof such as the reference surface 45 of the guide body 12, is located in the desired position that was previously determined in step 203. This can involve rotatably adjusting the positioning block 10 relative to the bone element, using the CAS system to aid in the correct orientation in each rotational axis of rotation. Three rotational degrees of freedom are thereby possible, and the entire positioning block 10 can be oriented in a desired plane, for example parallel to the distal cut to be made in the femur. Step 205 can also include proximally displacing the positioning block 10 in the direction 43 such that the proximal surface 45 is translated from a position shown in FIG. 4a to a position shown in FIG. 4b, abutting the femur 39. As the head 31 of the polyaxial screw 25 is distally spaced from the condyles 41 of the femur 39, the positioning block 10 requires a reference point with respect to the bone such that the location of the distal cutting guide, which will be fixed to the positioning guide block, will correctly correspond to the amount of bone which must be resected by the distal cut.

The proximal-distal translation of the guide block body 12 relative to the mounting member 14 greatly simplifies the referencing of the guide block with the femur. As the mounting member 14 is engaged in place on the head of the polyaxial screw, it is fixed in a proximal-distal direction relative to the bone. However, as the guide block body 12 can axially slide relative to the central mounting member 14 when the locking screw 34 is disengaged, the tracked guide body portion 12 remains rotationally fixed relative to the mounting member but can translate in the proximal-distal direction 43. This permits the guide body 12 to be proximally displaced until its proximal surface 45 directly abuts the most distal end of the condyles 41, as shown in FIG. 4b. By tightening the locking screw 34, the guide body 20 is retained in place on the central mounting member 14. The conical screw 33, as seen in FIG. 3, when tightened, fixes the positioning block 10 in place on the head 31 of the polyaxial screw 25, thereby fixing the reference surface 45 in the chosen desired position. The distal end of the femur, which is accurately located by the tracked guide body 20 that is located by the CAS system, can then be used as a reference plane, from which the resection depth can be easily measured. The amount of bone resected often varies as a function of the type of implant line being used, and the specific structure of the patient anatomy.

Further adjustment is also possible with the present universal positioning block assembly 10. Step 205 of FIG. 12 also comprises translation of the entire positioning block assembly 10 relative to the polyaxial screw 25, and therefore relative to the femur, in the anterior-posterior direction 47. By rotating the screw head 30, the mounting member body 20, shown in FIG. 2, and consequently the entire guide block body 12 are displaced relative to the fastener mount element 24 that is fixed to the polyaxial screw head 31. This affords substantially vertical adjustment of the positioning block if required by the specific procedure or the anatomy of the patient being operated. The positioning block can therefore be adjusted in five degrees of freedom, namely rotation about three rotational axes and translation along two perpendicular axes, namely in directions 43 and 47.

Once the desired position and orientation of the positioning block 10 is achieved, step 207 is performed, which comprises using the positioning block 10, and more particularly the reference surface 45, to locate a cutting tool, such as a drill or a saw, in a predetermined location, a known distance away from the reference surface 45, in order to make a hole or cut in the bone element at the predetermined location, as required by the implant being installed.

Figure 7:
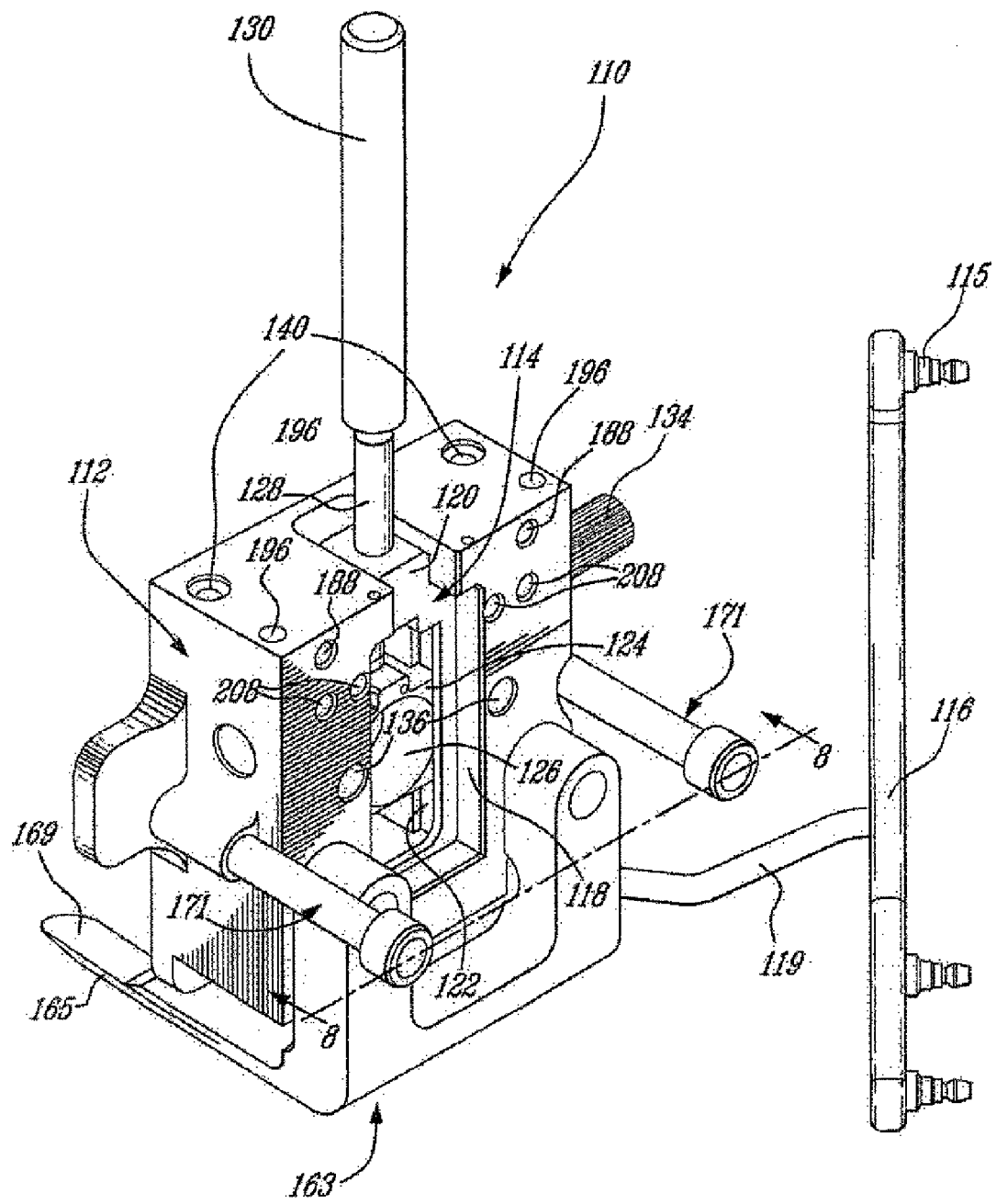
FIG. 7 is a perspective view of an alternate embodiment of a trackable CAS universal positioning block according to the present invention for use in total knee replacement surgery.
Figure 8:
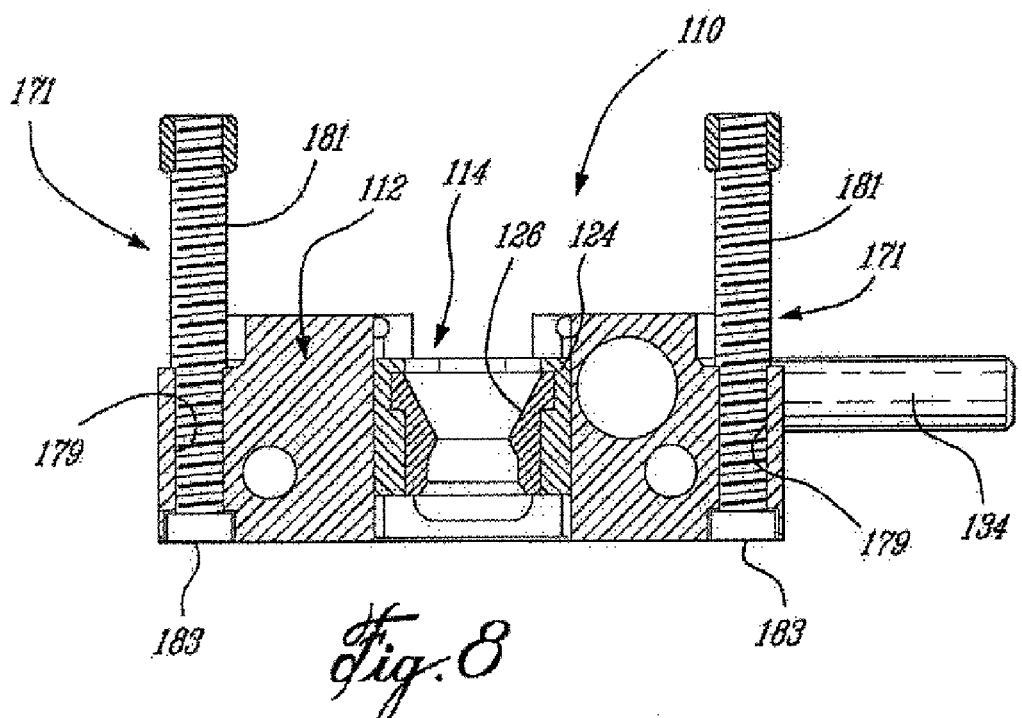
FIG. 8 is a cross-sectional view taken through line 8-8 of FIG. 7.

The universal positioning block assembly 110 of FIGS. 7 and 8, is similar to the guide block assembly 10, however comprises several additional features. Referring to FIG. 7 and FIG. 8, the universal positioning block assembly 110 comprises generally a guide body 112, a mounting member 114 and a tracker member 116. The tracker member 116 is preferably engaged with the guide body 112 via a mounting stem 119 and comprises at least three mounting posts 115 thereon for retaining trackable elements which are locatable by the CAS system. The mounting member 114 can translate relative to the guide body 112 within a central aperture 118. The mounting member 114 is captive within the central aperture 118, being retained therein by the closed end of the aperture 118 at one end and by retention pins (not shown), which prevent the complete removal of the mounting member 114 at the opposing end of the slot comprising the central aperture 118. A locking screw 134 extends through the guide body 112 for frictional engagement with a surface of the mounting member 114, for fixing the mounting member 114 in place such that relative movement between the mounting member 114 and the guide body 112 is substantially prevented. All individual parts of the universal positioning block assembly 110 are preferably retained captive with the block guide body 112. This eliminates the possibility of any small pieces becoming detached during surgery or being lost should a small part be dropped, for example. Drill guide holes 136 extend transversely through the guide body 112, and a pair of peg holes 140 are disposed on an upper surface of the guide body 112, permitting engagement with another drill/cutting guide block for example. The mounting member 114 comprises an independent adjustment mechanism including a fastener receiving mount element 124, which slides within a central slot 122 disposed within the mounting member body 120, and is translated therein by adjustment screw 128 which is manually actuated via screw head 130. The fastener receiving mount element 124 comprises an aperture 126 for engaging the substantially spherical head of the polyaxial screw 25.

As best seen in FIG. 8, the aperture 126 preferably includes opposed concave recessed portions, comprising a first substantially frusto-conical portion and a subsequent enlarged region capable of receiving the head of the polyaxial screw 25 therein. This permits the fastener receiving mount element 124 to be snapped into engagement with the head of the polyaxial screw 25, such that the fastener receiving mount element 124 can be held in position but nevertheless can be rotated relative to the polyaxial screw 25 without being fixed relative thereto. As described above, the guide body 112 can then be translated relative to the fastener receiving mount element 124 within the central aperture 118. The guide body 112 is displaced along a proximal-distal axis when the positioning block assembly 110 is engaged to a distal end of a femur. Friction locking screw 134 extends through the side of the guide body 112 and engages the mounting member 114, such that it can be retained in a selected position relative to the guide body 112. The fastener mount element 124 is displaced relative to the mounting member body 120 by endless screw 128, engaged to the fastener mount element 124 and extending through the mounting member body 120. The translation screw 128 is actuated by a screw head 130, such that rotation of the screw head 130 causes the fastener mount element 124 to be translated within the guide slot 122. The translation, or elevation, screw 128 thereby enables the entire positioning block guide body 112 to be raised or lowered along an anterior-posterior axis when engaged to a distal end of a femur.

The universal positioning block assembly 110 further comprises at least two independent adjustment mechanisms that are adjustable in substantial isolation for adjustably displacing the cutting tool guide element or guide body 112 in one of at least two degrees-of-freedom. The independent adjustment mechanisms preferably include two adjustment screws 171, adapted for adjustment of the Varus-Valgus angle. The Varus-Valgus adjustment screws 171, best seen in FIG. 8, have outer threads 181 for threaded engagement with holes 179 in the guide body 112 and include substantially flat end faces 183 for pressed contact with the bone surface, such as the distal ends-of the femoral condyles for example. The Varus-Valgus adjustment screws therefore permit fine tuned angular adjustment of the universal positioning block assembly 110 relative to the bone element about a substantially vertical axis, when the universal positioning block assembly 110 is fastened to the distal end of the femur for example. This permits more accurate location of the universal positioning block assembly 110, in comparison with manual adjustment of the assembly until the correct Varus-Vargus angle is achieved. These adjustment screws therefore permit the universal positioning block assembly 110 to be accurately adjusted on the polyaxial screw in a single rotational degree of freedom, as guided by the CAS system. This helps simplify the multiple-degree of freedom adjustment required to position the universal positioning block assembly 110 in the desired final position.

The universal positioning block assembly 110 also comprises a posterior condyle palpator 163, which can be used to better centrally locate the universal positioning block assembly 110 when engaged to the polyaxial screw 25 fastened to the distal end of the femur. The posterior condyle palpator 163 is generally L-shaped, being engageable to the positioning block guide body 112 via mounting pins which engage corresponding holes within the outer face of the positioning block guide body 112, and having leg portions 165 extending generally away from the positioning block guide body 112, in a proximal direction when the universal positioning block assembly 110 is engaged to a distal end of a femur. The extending leg portions 165 include generally flat palpating regions 169 for abutting the posterior surfaces of the femoral condyles. In this way, the universal positioning block assembly 110 can be consistently mounted on the femur such that it is substantially vertically positioned. Ideally, the polyaxial screw 25 is vertically located at about one third of the anterior-posterior distance from the anterior surface of the distal end of the femur, meaning the universal positioning block assembly 110 will be ideally vertically located more anteriorly than posteriorly on distal end of the femur. The exact location, however, will depend largely on the particular anatomy of each patient, which can greatly vary. This will increase the likelihood that the anterior-posterior adjustment range permitted by the translation screw 128 will be sufficient. Additionally, with the leg portions 165 of the posterior condyle palpator 163 abutting the posterior condyles of the femur, a pivot point is temporarily created about the contact points. When the translation screw 128 is rotated, the entire guide body 112 of the universal positioning block assembly 110 is translated relative to the mounting member 114 engaged with the polyaxial screw 25, and is therefore forced to pivot about a substantially horizontal axis defined between the contact points between the generally flat palpating regions 169 and the femoral condyles. This enables the controlled adjustment of the universal positioning block assembly 110 about a substantially medial-laterally extending horizontal axis.

Therefore, both the posterior condyle palpator 163 and the Varus-Valgus adjustment screws 171 help permit the controlled and precise adjustment of one rotational degree of freedom. This greatly simplifies the adjustment of the position and orientation of the universal positioning block assembly 110 in space. Using the CAS system, each of the rotational and translational degrees of freedom can be individually adjusted into a predetermined position or orientation, to achieve the desired final position and orientation of the universal positioning block assembly 110 relative to the bone element. The user can identify to the CAS system what the desired final position and orientation of the universal positioning block assembly 110 relative to the bone element should be, and the CAS system can subsequently prompt the user to vary each of the degrees of freedom independently as required.

The five degree of freedom adjustment that is possible by the positioning block assembly 10,110 permits it to be universally used in total knee replacement surgery, regardless of the type of implant line being used and of the surgical steps to be performed. It can be used, for example, in conjunction with a cutting guide to create the distal Gut required for femoral implant preparation.

Figure 5A:
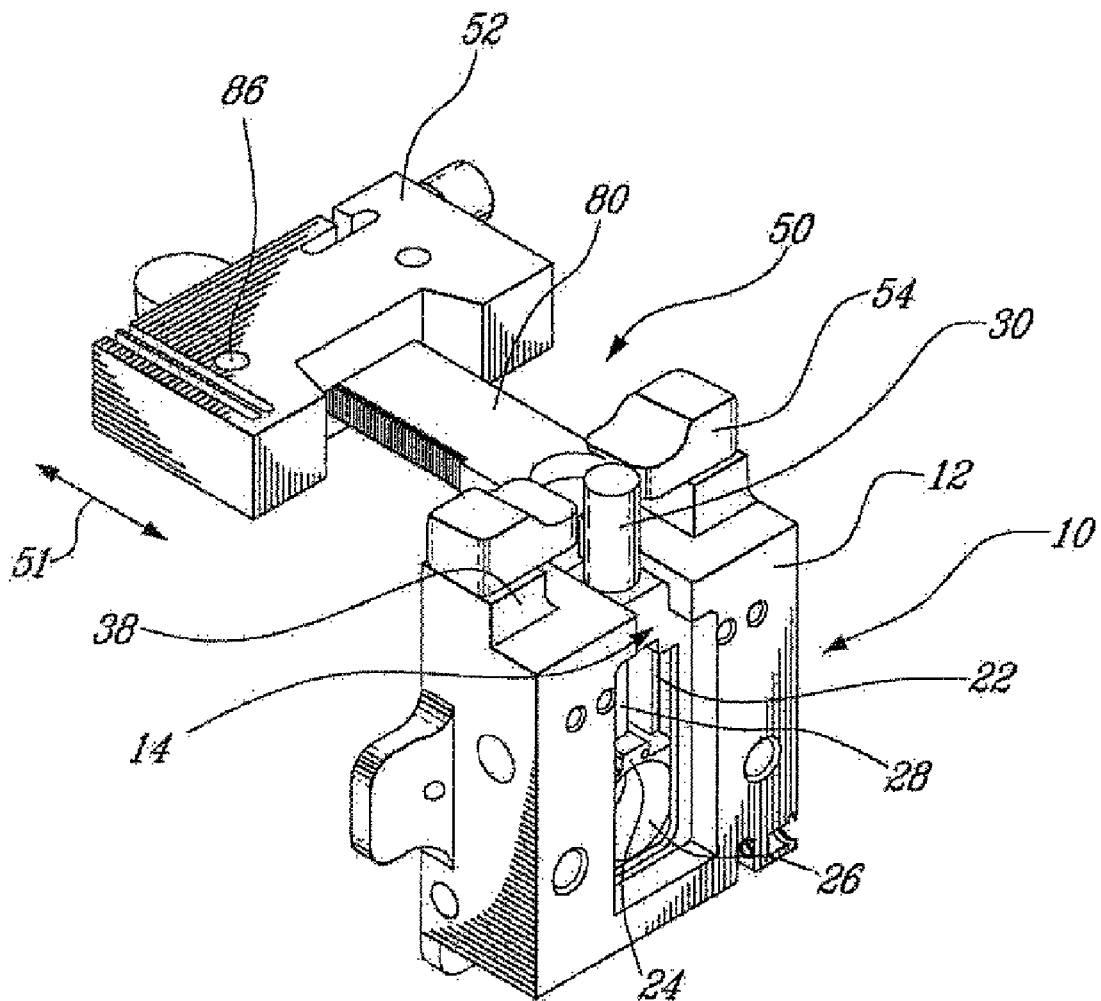
FIG. 5a is a perspective view of the CAS universal positioning block of the present invention assembled with a distal drill/cutting guide block.

FIG. 5a shows the universal positioning block 10 having a distal pin drill guide assembly 50 mounted thereto, which is more fully described in U.S. Provisional Patent Application Ser. No. 60/405,353, filed Aug. 23, 2002, the contents of which are incorporated herein by reference. The distal pin drill guide assembly 50 generally comprises an anterior guiding platform 54 and a displaceable drill guide block 52. The anterior guiding platform 54 includes locating pegs which mate with the peg holes 40 in the two mounting points 38 of the positioning guide body 12, and a proximally extending elongated tongue portion 80 on which the grill guide block can slide. The drill guide block 52 is preferably sized such that when fully abutted against the anterior guiding platform 54, the location of the pin drill holes 86 correspond to the location required for the locating pins which are inserted into the femur to secure the distal cutting guide block in the precise position such that the required amount of bone is resected by the distal cut. However, the drill guide block 52 can be proximally displace along the anterior guiding platform 54, and selectively fixed in position thereon. Knowing the position of the positioning guide block 12, abutted with the distal end of the femur, the CAS system can indicate to the surgeon exactly how far along the anterior guiding platform 54 the drill guide block 52 is to be displaced, such that the distal cutting guide pin holes 86 can be used to create drilled holes in the bone at the necessary position. The CAS system can indicate this graphically, or indicate numerically how many notches or graduations the drill guide block 52 is to be translated along the elongated tongue portion 80 of the guiding platform 54. The system can also simply indicate at which final demarcation the drill guide block 52 is to be located, thus avoiding the surgeon having to count the number of graduation or notches that the drill guide must be moved by.

Alternately, as shown in FIG. 5b, a conventional femoral distal cutting guide block 59 can be engaged directly to the universal positioning block 10, via an alternate tool guide guiding platform 55, which similarly mates with the positioning block 10 and comprises proximally extending mounting pegs 57, to which the cutting guide block 59 can be mounted. A thumb-screw 61 is provided to engage the cutting block 59, such that it can be pulled towards the proximal face of the universal positioning block body 12, and positioned at the exact distance required from the proximal face of the positioning block 10 abutted to the distal end of the femur, which will correspond to the amount of condyle resected by the distal cut made using the cutting block 59 as a guide.

It is to be understood that the alternate universal positioning block assembly 110 can similarly be used in conjunction with the distal pin drill guide assembly 50 and the conventional femoral distal cutting guide block 59, as respectively shown in FIGS. 5a and 5b. It is to be understood that the alternate universal positioning block assembly 110 can similarly be used in conjunction with the distal pin drill guide assembly 50 and the conventional femoral distal cutting guide block 59, as respectively shown in FIGS. 5a and 5b. While the positioning block assembly 10 is shown without a trackable member 16 in FIG. 5a, it is to be understood that the universal positioning block assembly 10 is preferably used in conjunction with an image guided computer assisted surgical system, capable of locating the detectable elements 17 of the trackable member 16, such as shown in FIG. 5b, such that the position and orientation of the universal positioning block can be determined and displayed by the CAS system relative to the anatomical structures of the patient. However, the present universal positioning block 10,110 can equally be used in conventional non-computer assisted surgery, wherein the five degrees of freedom adjustment of the universal positioning block can similarly permit more precise alignment of surgical tool guides engaged to the positioning block assembly 10,110.

The drill guide holes 36 located in the guide body 12 of the positioning block assembly 10,110 permit the femoral implant peg holes to be drilled in the distal end of the femur. As the proximal face 45 of the positioning block 10 can be directly abutted against the most distal point of the condyles, the depth of the peg holes which must be drilled can be calculated, knowing the distance to be resected by the distal cut. For example, if the peg holes are to be made 5 mm deep and 10 mm of bone is to be resected by the distal cut, then 15 mm deep peg holes can be drilled using the drill guide holes 36 before the distal cut is made. As selected additional anterior-posterior adjustment is possible if required using the translation screw 28 of the mounting member 14, the implant peg holes can be accurately aligned regardless of their position relative to the bone mounting screw. By enabling the proximally directed implant peg holes to be drill before the distal cut is made, several surgical steps can be avoided, thereby significantly simplifying the procedure required to perform total knee replacement surgery using a CAS positioning guide block. The posterior condyles palpator 163 of the universal positioning block assembly 110, may also aid in correctly locating the position of the femoral implant peg holes which are drilled into the distal end of the femur.

Although the universal positioning block assembly 10,110 has been described above with emphasis on the preparation of the femur for receiving the femoral portion of a knee replacement implant, the universal positioning block assembly 10,110 is also used for the preparation of the tibia for the corresponding tibial portion of a knee replacement implant. The steps required to prepare the tibia, include: defining the tibial mechanical axis; using the universal positioning block assembly 10,110 to determine a desired rotational alignment of the guide block and fastening it in place to the anterior surface of the proximal end of the tibia using the polyaxial screw 25; adjusting the guide block to ensure a desired posterior slop and level of tibial resection; inserting location pins using the guide block; removing the guide block and replacing it with a tibial resection cutting guide that is retained in place with the location pins; and resecting the chosen amount of tibial bone.

Figure 9:
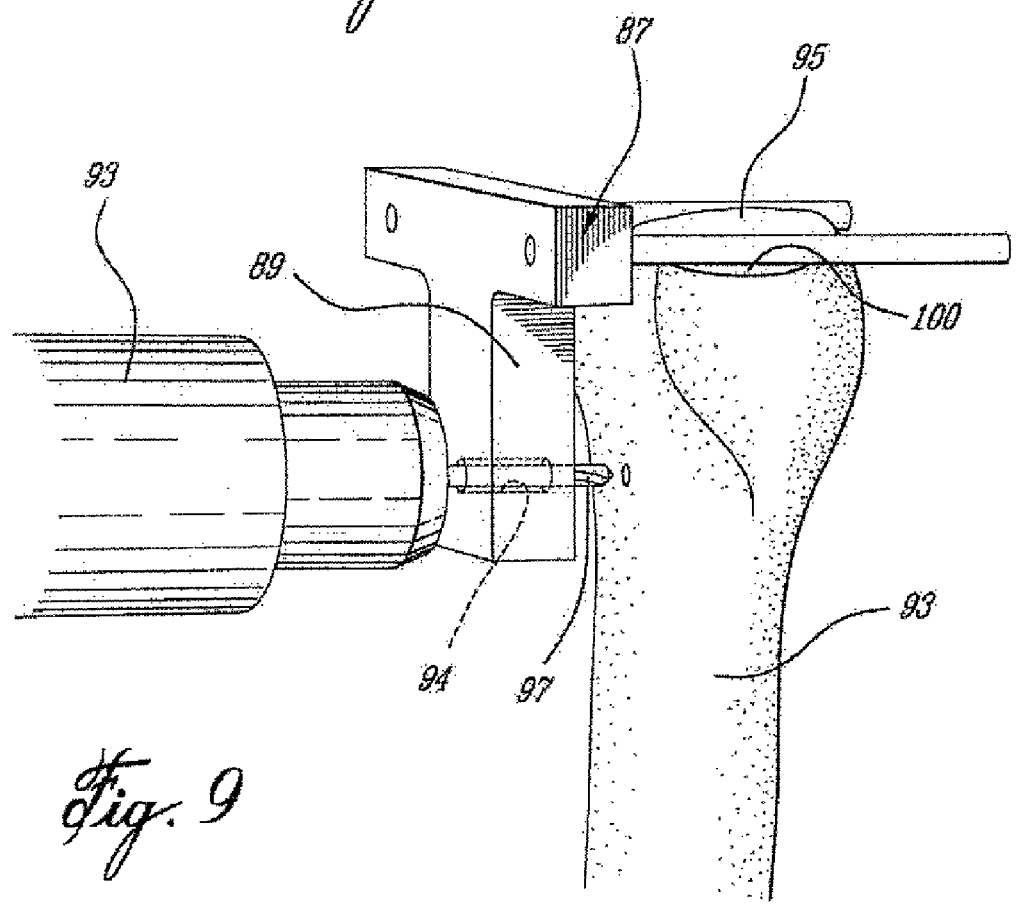
FIG. 9 is a perspective view of a tibial polyaxial screw drill guide for use with the present invention.

As correctly locating the entry point of the polyaxial screw into the tibia can be sometimes problematic and time consuming, the tibial polyaxial screw drill guide 87, as shown in FIG. 9, is preferably used to drill a pilot hole in the correct location for the polyaxial screw placement. The tibial polyaxial screw drill guide 87 comprises a main body 89 and two locating pins 91 extending from an upper portion of the main body 89. A drill guide hole is disposed in the main body 89 at a specified distance away from the locating pins 91. Each locating pin 91 is adapted for resting on the proximal end of the tibia 93, on the tibial plateaus 100 on either side of the tibial tuberosity 95. The bit 97 of the drill 99 can then be inserted through the drill guide hole 94 in the main body 89, and a pilot hole for the polyaxial screw can be easily created in the correct location in the tibia. As a general guide, the drill guide hole 94 in the main body 89 is preferably provided at a position relative to the bottom of the locating pins 91, and therefrom from the surface of the tibial plateau.

Figure 10A:
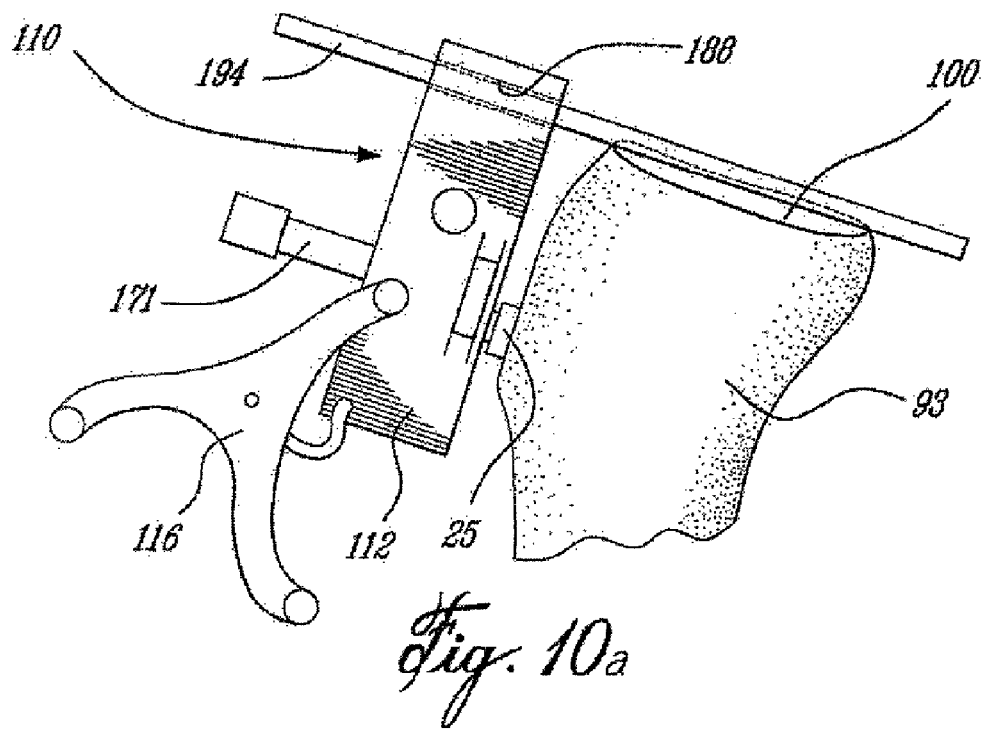
FIG. 10a is a side elevation view of the universal positioning block of FIG. 7, used in conjunction with tibial posterior slope matching alignment pins.

Referring now to FIG. 7 and FIG. 10a, with regards the use of the universal positioning block assembly 110 for the preparation of the tibia 93 for the knee implant, the universal positioning block assembly 110 comprises a pair of transversely extending alignment holes 188 that extend transversely through the guide body 112. These alignment holes 188 are used for matching the posterior slope of the tibial plateau with the orientation of the universal positioning block assembly 110. With the universal positioning block assembly 110 engaged to the tibia 93 by the polyaxial screw 25 such that the universal positioning block assembly 110 can be rotated relative thereto, the two alignment pins 194 are inserted into the alignment holes 188, as shown in FIG. 10a. The alignment pins 194 are used to rest on top of the sloped posterior tibial plateau 100 such that the posterior-anterior angle of the universal positioning block assembly 110 corresponds to the posterior slope of the tibia.

Figure 10B:
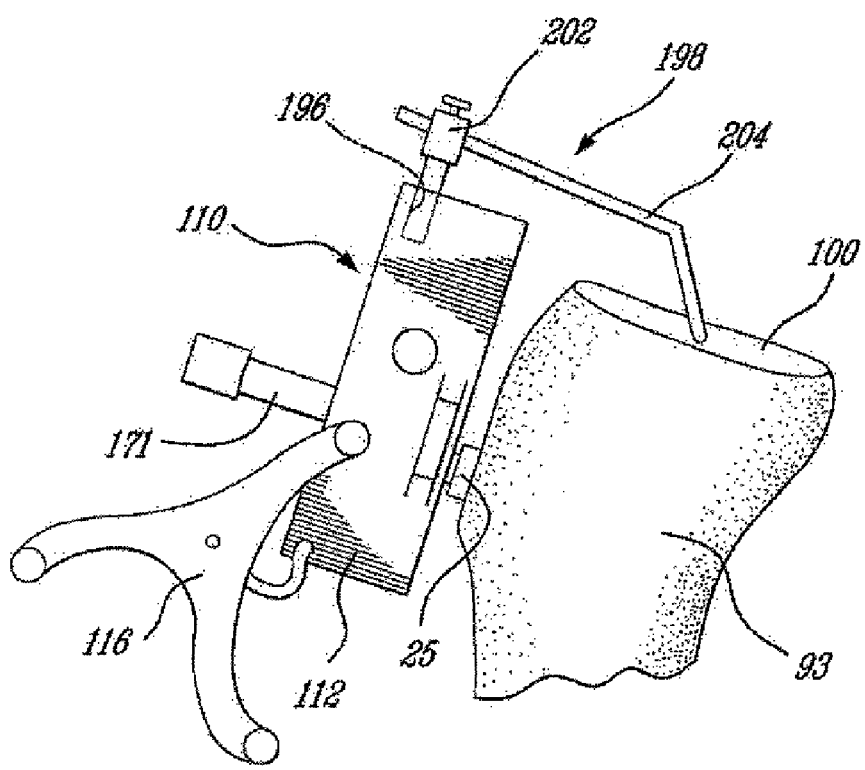
FIG. 10b is a side elevation view of the universal positioning block of FIG. 7, used in conjunction with a tibial positioning stylus.

The universal positioning block assembly 110 is further engageable with another adjustment simplification device for use when using the universal positioning block assembly 110 with the tibia 93. As best seen in FIG. 7, the universal positioning block assembly 110 includes a pair of threaded, longitudinally extending positioning stylus engagement holes 196. As shown in FIG. 10b, these engagement holes 196 are adapted for engaging a tibial positioning stylus 198 to the universal positioning block assembly 110. The tibial positioning stylus 198, comprising an adjustable support member 202 and an elongated stylus element 204, is used to help locate the universal positioning block assembly 110 in a desired position relative to a proximal end of the tibia 93, such as a tibial plateau 100.

Once all the necessary adjustments of the universal positioning block assembly 110 are made and it is positioned as required relative to the tibia 93 using the CAS system and the abovementioned adjustment tools, the conical screw 35 of the polyaxial screw 25 is tightened, fixing the universal positioning block assembly 110 in place. The tibial cutting guide pins holes can then be drilled in the tibia 93 using the necessary guide holes 208 in the guide body 112, best seen in FIG. 7, and the pins can be inserted through the guide holes 208 and into the tibia. The entire universal positioning block assembly 110 can then be removed, and a tibial cutting guide block can be installed onto the pins, and the tibial cut can be made to resect the chosen amount from the proximal end of the tibia 93.

Figure 11A:
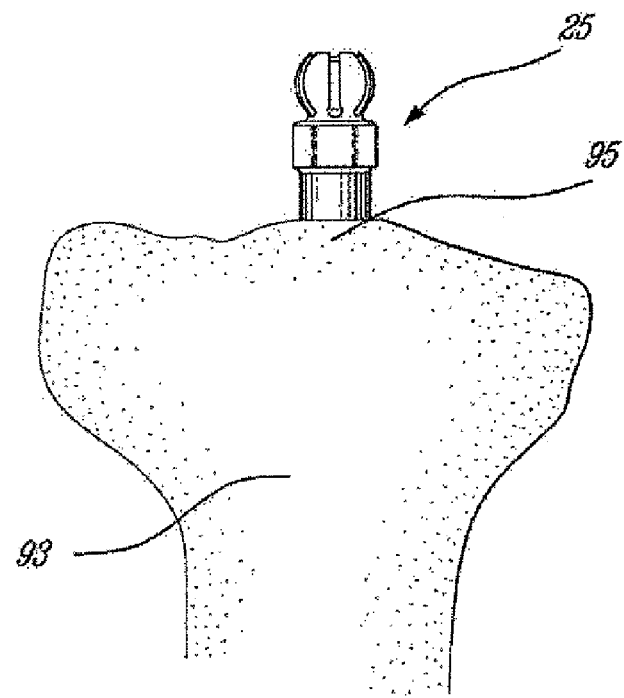
FIG. 11a is a front elevation view of the polyaxial screw alternately mounted in the tibia.
Figure 11B:
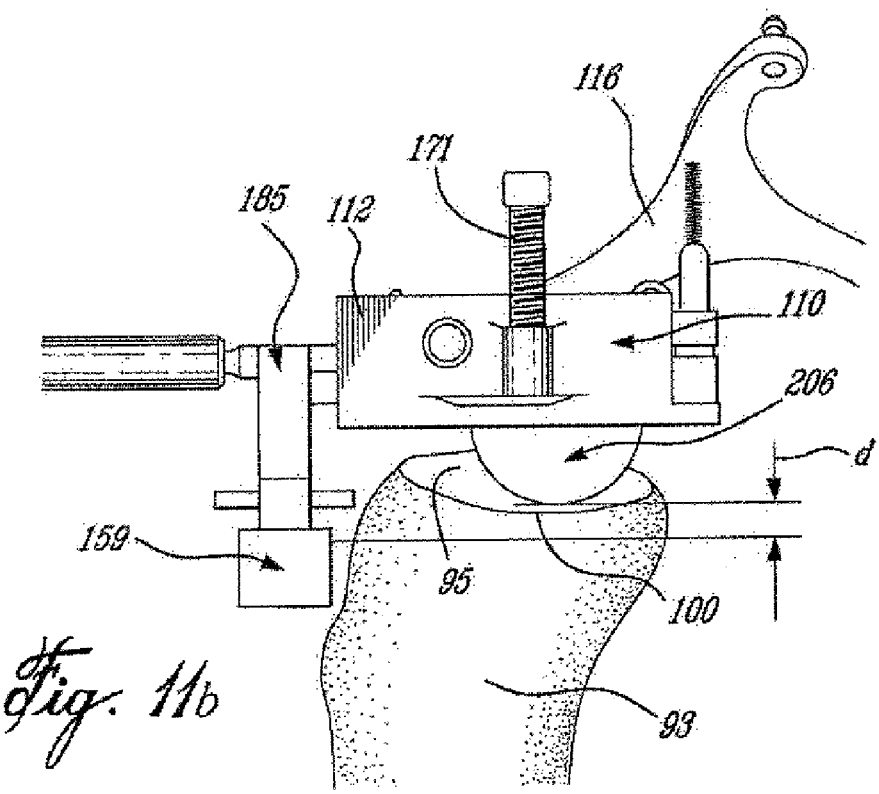

In an alternate technique for mounting the universal positioning block assembly 110 to the tibia, the polyaxial screw 25 is inserted in the intercondylar tubercle 95 of the tibia 93, as seen in FIG. 11a, parallel to the mechanical axis of the tibia. This is in contrast to the above described method, as illustrated in FIGS. 10a-10b, where the polyaxial screw is inserted into the tibia perpendicularly to the tibial mechanical axis, on an anterior surface thereof. Referring to FIG. 11b, the universal positioning block assembly 110 can then be engaged to the polyaxial screw 25 such that it is oriented substantially parallel to the desired tibial cut to be made. This alternate mounting arrangement permits the tibial cutting guide block 159, fixed to the universal positioning block assembly 110 via a tibial cutting block support 185, to be pined directly to the tibia 93 without removal of the universal positioning block assembly 110 and other CAS equipment. Particularly, the translating mounting member 114 of the universal positioning block assembly 110, permits the guide body 112 to be lowered relative to the fixed polyaxial screw 25 such that the tibial cutting block 159 is lowered to a desired resection level. Preferably, a spacer 206 is used as shown in FIG. 11b. Based on the dimensions of the tibial cutting guide block support 185, the spacer 206 is sized such that the required distance "d", between the deepest point of the tibial plateau 100 and the resection cut to be made, corresponds to the distance between the spacer 206 and the cutting guide slot in the tibial cutting guide block 159. This distance "d" is defined by the implant to be used. For example, when using Natural-Knee® II type implants, this distance should be approximately 7 mm (about 0.276 inches).

In an alternate embodiment, the insertion of the polyaxial screw 25 into the femur 39 or the tibia 93 can be done using a trackable screwdriver. The GAS system, knowing the position of the screwdriver and therefore the polyaxial screw 25, can therefore determine the proximal-distal position that the polyaxial screw 25 must be positioned in, such that the positioning block 10,110 will be positioned in a chosen position relative to the femur 39, when the positioning block 10,110 is engaged thereto. For example, when the shoulder 27 of the polyaxial screw 25 reaches the correct position, the CAS display indicates that the screw has been inserted to the precise depth required for the proximal face of the positioning block 10,110, when engaged on the polyaxial screw 25, to abut the most distal point of the femur 39. The positioning block 10,110 can the be snapped onto the head 31 of the polyaxial screw 25, and rotatably adjusted as described above. This permits the translation of the positioning block 10,110 relative to the femur 39 in the proximal-distal direction to be eliminated if required.

The distal pin drill guide assembly 50 as shown in FIG. 5a will now be described in further detail. The distal pin drill guide assembly 50 can equally have a cutting guide slot, such that the guide assembly can be used as a distal cutting guide to resect bone from the condyles of the femur prior to installation of a femoral implant. It is also to be understood that the guide block can be used as a drill guide for creating other holes than those for locating pins for a distal cutting block used in the femoral preparation for a implant in knee replacement surgery. Additionally, while the distal pin drill guide assembly 50 is intended for use with the positioning block 10 in total knee replacement surgery, an equivalent structure can also be used for any surgical application where one moveable element must be precisely translated a selected distance relative to another fixed element.

Figure 15:
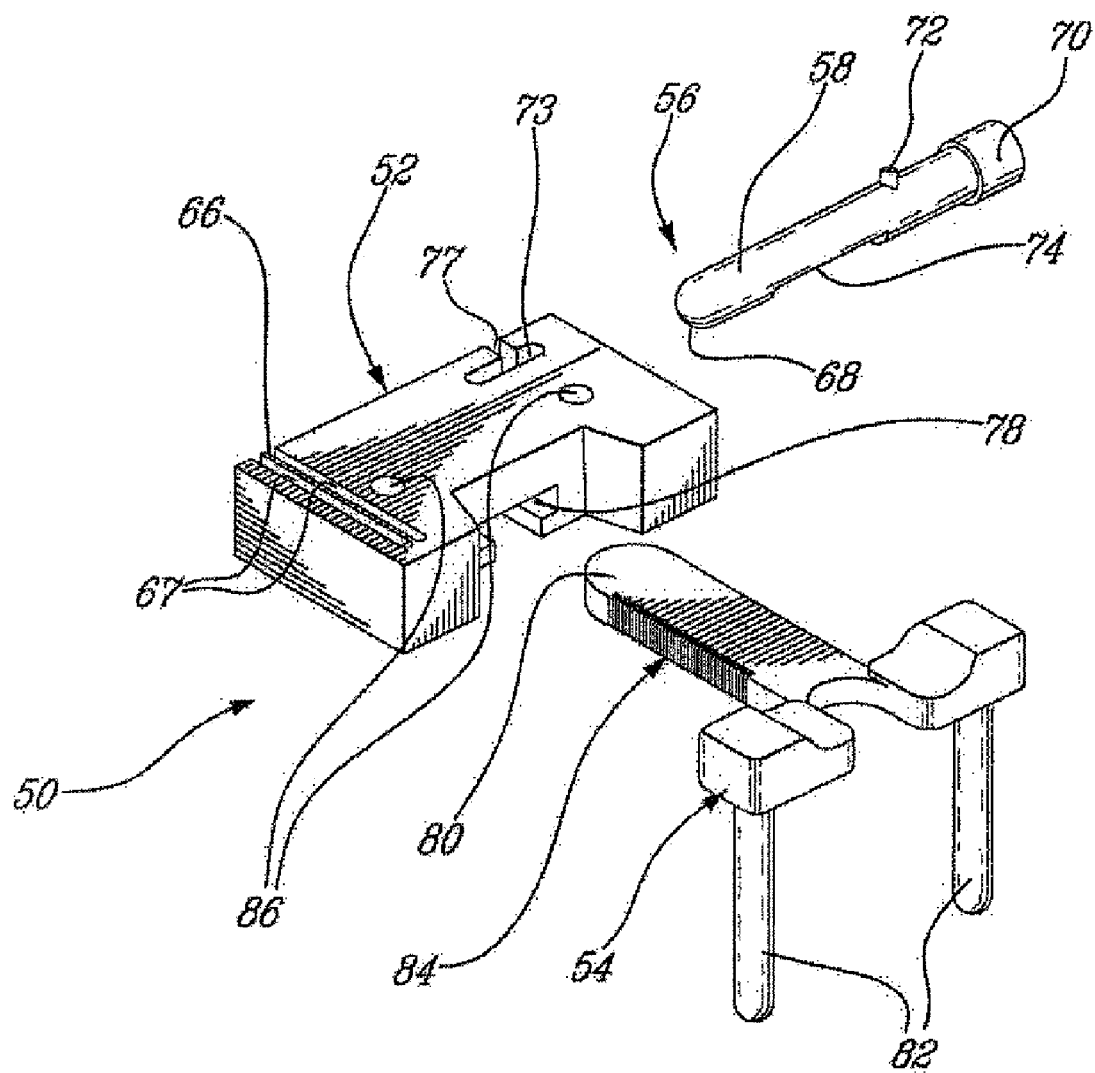

Referring now to FIG. 15, the surgical tool guide 50, particularly a distal pin drill guide assembly in the preferred embodiment, comprises a guide block 52 and a anterior guiding platform 54. The drill/cutting guide block 52 comprises a central slot 78 for receiving the tongue portion 80 of the guiding platform 54, such that the guide block is translatable along the tongue portion 80, thereby permitting relative displacement therebetween. The anterior guiding platform 54 comprises fixation pegs 82, which in the preferred embodiment, are adapted for engagement with the universal positioning block 10 fixed directly to the femur, generally intramedullary mounted thereto using a polyaxial or standard bone screw, or another similar fixation method. In this case, the drill/cutting guide block 52 is enabled to slide in the proximal-distal direction, over the anterior surface of the distal end of the femur.

Figure 16A:
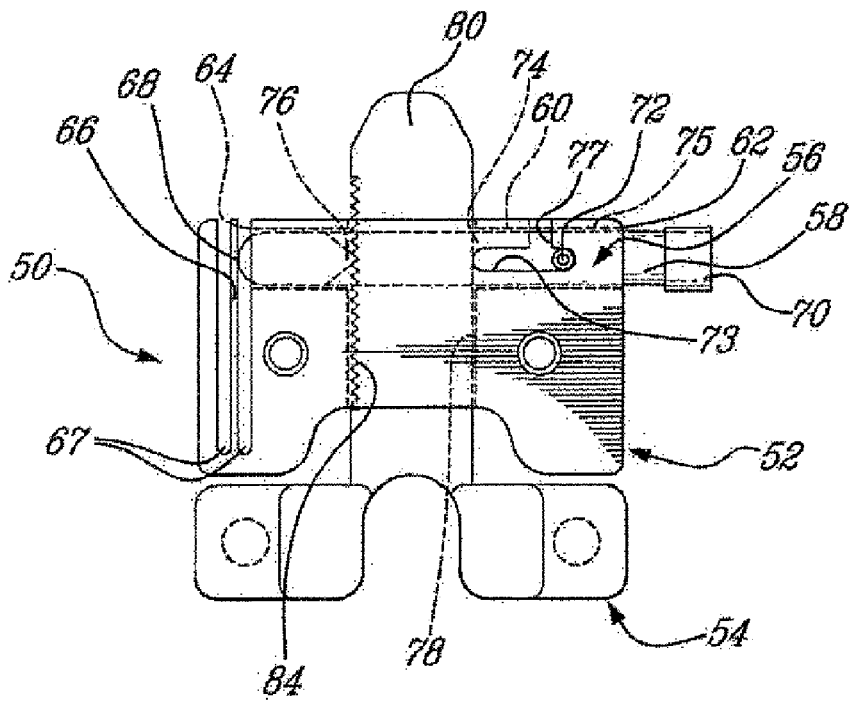
FIG. 16a is a top elevation view of the surgical tool guide as shown in FIG. 15, wherein the position locking mechanism is engaged, thereby fixing the guide block in place on the guiding platform.
Figure 16B:
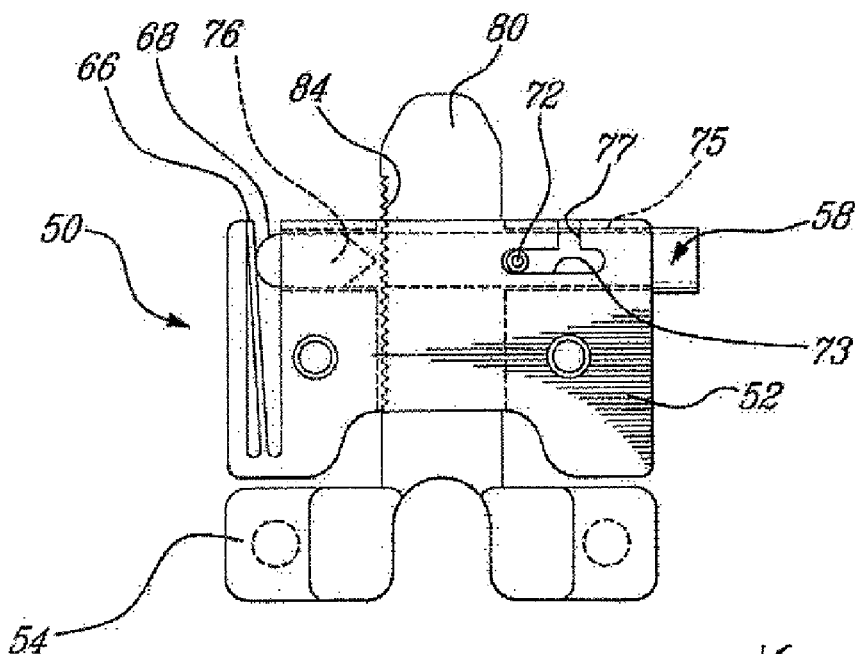
FIG. 16b is a top elevation view of the surgical tool guide as shown in FIG. 15, wherein the position locking mechanism is released, thereby permitting movement of the guide block on the guiding platform.
Figure 17A:
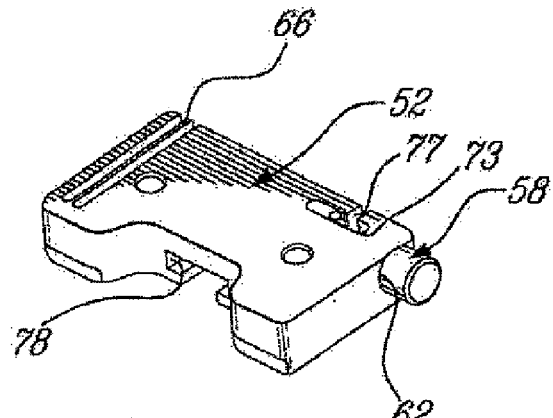
FIG. 17a is a perspective view of the distal drill/cutting guide block as shown in FIG. 15 with the plunger engaged therein.
Figure 17B:
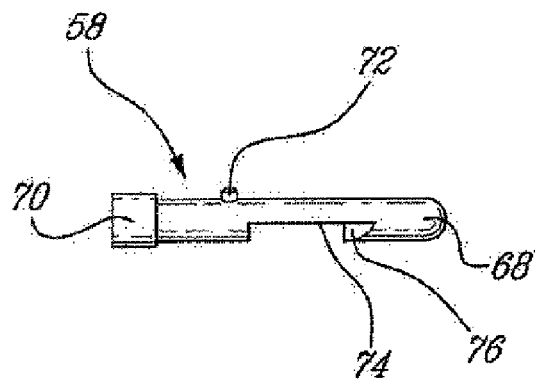

As seen in FIGS. 16a, 16b and 17a, the guide block 52 comprises a biased locking mechanism 56, used to locate the guide block 52 on the guiding platform 54, which generally includes an outwardly biased, semi-captive plunger 58 which fits within a transversely aligned cylindrical socket 60 in the guide block. The blind socket 60 comprises a first open end 62 in one side of the guide block and a blind second end 64. A blade spring 66, preferably integrally formed in the guide block by machining two parallel axially aligned slots 67 therein, intersects the socket 60 near the second end 64 thereof. The plunger 58, best seen in FIG. 17b, is therefore the only discrete element of the mechanism, and comprises an outer end 70, an inner end 68, a locating pin 72 radially projecting from the substantially cylindrical plunger at a point therebetween, and a central inner flat slot portion 74 formed through one edge of the plunger and corresponding to the slot 78 formed through the guide block. A pawl 76 is integrally formed in the plunger such that the point projects into the slot 74 of the plunger.

Figure 17C:
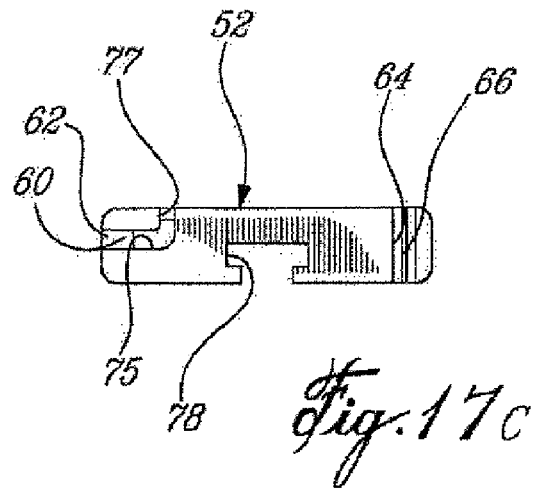

Referring to FIGS. 17a, 17b and 17c, the plunger 58 is inserted into the socket 60 by aligning the pin 72 with a transverse pin slot 75 disposed along a front side of the guide block, once the pin blocks any further transverse movement of the plunger, the pin 72 can pass through axially directed slot 77 which joins the side transverse slot with a top transverse slot 73, such that the plunger can be rotated ninety degrees. The alignment pin 72, which is retained within the transverse top pin slot 73, thereby limits the transverse movement of the plunger as it slides within the socket 60 of the guide block. As the blade spring 66 forces the plunger 58 outwards, the pin 72 can not readily slide out of the top pin slot 73. The plunger is therefore securely retained within the socket. However, removal of the plunger from the socket, when required, is nevertheless a simple and quick procedure. The outer end 70 of the plunger 58 is depressed enough such that the alignment pin 72 is adjacent the axially directed top slot 77, perpendicular to the top transverse slot 73. The plunger is then rotated about itself approximately ninety degrees, such that the pin passes through the slot 77 and into the front transverse pin slot 75 which horizontally extends between the vertical slot 77 and the edge of the block. The plunger 58 can then be completely slid out of the socket 60.

This pin and slot engagement system therefor permits easy installation and removal of the plunger within the guide block, while nevertheless securely retaining the plunger therewithin and limiting its movement by providing inner and outer stops. The inner end 68 of the plunger engages the blade spring 66, such that the blade spring provides a spring force against the plunger, biasing it outwards. When the plunger is installed in position within the socket, the plunger is normally biased outwardly such that the pin 72 is at the outer end of the slot 73 and the pawl 76 projects into the slot 78 of the guide block, as shown in FIG. 16a. The pawl 76 engages notches 84 disposed along one edge of the tongue 80 of the anterior guiding platform 54 when it protrudes into the slot 78 of the guide block through which the tongue 80 passes. This prevents any movement of the guide block 52 on the guiding platform 54. When the outer end 70, of the plunger 58, that protrudes beyond the edge of the guide block is depressed, thereby acting against the blade spring 66, the pawl 76 of the plunger is retracted into the socket such that it no longer projects into the slot 78 of the guide block and therefore into the notches 84. As long as the outer end of the plunger is depressed, as shown in FIG. 16b, the guide block 52 is permitted to slide along the tongue 80 of the guiding platform 54. However, as soon as the end of the plunger is release, the blade spring forces the pawl portion 76 of the plunger back into one of the notches 84. The blade spring therefore normally retains the pawl engaged in a notch 84, such that the guide block 52 is retained in place on the guiding platform 54.

Figure 18:
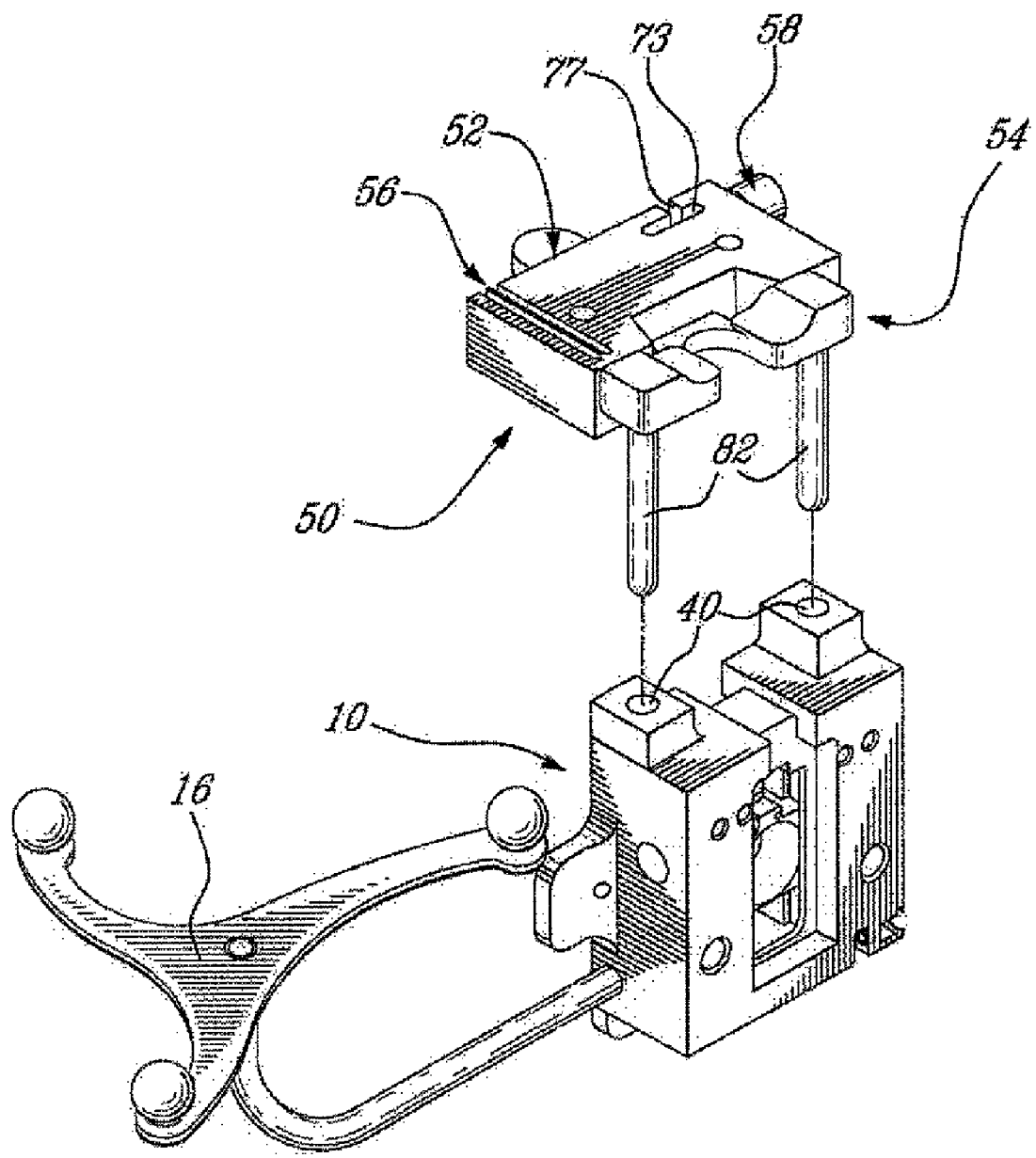
FIG. 18 is an exploded perspective view of the distal drill/cutting guide block of FIG. 15 and the CAS universal positioning reference block of FIG. 1.

Referring to FIG. 18, the locating pegs 82 of the anterior guiding platform 54 are preferably engageable with corresponding holes 40 in the universal positioning block 10. As described above, the positioning block 10 is aligned in a plane parallel the distal cut to be made, and secured in place. With the positioning block in a known reference position relative to the most distal end of the femur, the exact distance that the distal drill/guide block 52 must be displaced along the anterior guiding platform 54 such that the correct amount of bone is resected by the distal cut is determinable. Preferably, the positioning block is directly abutted the most distal femoral condyle. The guide block 52 can then be located at a position along the anterior guiding platform, based on the type of implant being used, such that the pin drill holes or cut made using the guide block 52 are accurately positioned. The proximal-distal displacement of the guide block 52 on the anterior guiding platform 54 permitted by the disengageable locking mechanism 56, enables distal cuts of various resection amounts to be made as required. This femoral distal resection amount can vary as a function of the type of implant being used, or the specific anatomical structure of the patient. A plurality of graduations are provided along the tongue 80, preferably at 1 mm intervals. This permits accurate determination of the distance that the guide block is moved relative to the fixed positioning reference block. The same intervals also preferably correspond to the distance between each adjacent notch 84.

If the positioning block 10 is being used in conventional (i.e.: non-CAS) surgery, it does not require a trackable member 16, and therefore can be used as depicted in FIG. 5a. If the position relative to the bone, into which the positioning block 10 is aligned and fixed, is known or can be determined, then the distal drill/cutting guide block 52 can be displaced the required amount on the tongue 80 of the platform 54 relative to the fixed positioning block 10, thereby permitting drill holes or the distal cut to be created in the required locations.

While the drill/cutting guide block 52 of the surgical tool guide 50 can be used to create a distal cut in the femur as required for installation of an implant, the positioning block 10 of the present invention can also be used with standard cutting blocks or jigs typically used to perform the cuts required for the installation of a particular implant type. Various different knee replacement implants are currently used.

Generally, each implant type requires cutting guide blocks, used to create the distal and the anterior cuts in the femur and the tibial cut, which are specific to that particular implant. Accordingly, all reference guides used to correctly position the cutting guide blocks and CAS navigation systems have traditionally had to be either tailored to one specific implant type or had to include a plurality of adapters, each able to accommodate one implant-specific cutting guide block. Using either one of a universal distal cut adaptor and a universal anterior cut adapter, the positioning block 10 of the present invention, guided by the CAS total knee replacement system as described herein, can be used to position the distal and anterior cutting guide blocks of any implant type in the necessary position. Therefore, this permits knee navigation surgeries with any implant brand or cutting guide block type using the same instruments and the same CAS system.

The common element in all knee cutting jigs or guide blocks produced by the various implant manufacturers is the cutting reference surface used to guide the saw blade. Accordingly, the universal adapters of the present invention comprise a plate portion adapted to mate with the saw guide slot on any typical knee surgery cutting guide block.

Particularly, referring to FIG. 19, the universal distal cutting guide adaptor 350 is mounted to the positioning block 10 as described above. The universal distal cutting guide adaptor 350 engages a standard distal cutting guide block 352 corresponding to a given implant type, and is adapted to position the standard distal cutting guide block 352 in a desired location to make the distal resection of the femoral condyles. The universal distal cutting guide adaptor 350 comprises generally a plate portion 354 which is shaped to fit within the saw blade guide slots in most standard distal knee cutting guide blocks currently used in total knee replacement surgery. Two plate engaging posts 356 are fixed to the plate portion 354 at their proximal ends and extend generally perpendicularly therefrom. The distal ends of the plate engaging posts 356 mate with a plate positioning member 360, which is engaged to the positioning block 10 and which permits the plate portion 354 to be moved proximally or distally to be positioned at a given offset from the proximal reference surface on the positioning block 10. The plate positioning member 360 preferably permits predetermined incremental translation of the plate engaging posts 356 relative thereto. The plat positioning member 360 can therefore comprise a rack and pinion type mechanism, or a biased rack and pawl mechanism as described above with regards to the surgical tool guide 50.

Once the plate portion 354 is positioned at the predetermined location relative to the positioning block 10 using the plate positioning member 360, it can be tracked by the CAS system which is tracked the positioning block 10. The reference surface on the positioning block 10 can then be abutted against the femur, and the tracked plate portion 354 is accordingly then already positioned at the predetermined distal cut location required by the implant type being used. The standard distal cutting guide block 352 is then simply slid overtop of the plate portion 354 which inserts into the saw guide slot therein. The standard distal cutting guide block 352 can then be pinned in place on the femur. Once the standard distal cutting guide block 352 has thus been correctly positioned and pinned in place, the positioning block 10 and the universal distal cutting guide adaptor 350 attached thereto can accordingly be completely removed from the femur and the distal cut can then be made. This applies regardless of the type of standard distal cutting guide block 352 used, or the amount of resection required by the type of implant chosen.

Referring to FIGS. 20*a* and 20*b*, the universal anterior cutting guide adaptor 380 is similarly engaged to the top face of the positioning block 10, and used to locate a standard anterior cutting guide block 382 as shown in FIG. 20*b*. The universal anterior cutting guide adaptor 380 comprises a plate portion 384 which is fixed to the top of the positioning block 10 by thumb screws 388, the plate portion being sized to fit within the saw blade guide slot in most standard anterior cutting guide blocks 382. Accordingly, the location of the plate portion 384 will correspond to the location of the anterior cut made in the femur. As the plate portion 384 can be tracked by the CAS system because it is fixed in place on the tracked positioning block 10, the location of the anterior cut can be carefully aligned. The universal anterior cutting guide adaptor 380 also further includes a triangularly shaped block portion 386 which is adapted to be securely pinned in place on the anterior surface of the femur. Therefore, once the positioning block is located in the desired location to align the plate portion 384 as required, the block portion 386 can be pinned in place on the femur. The positioning block 10 and the universal anterior cutting guide adaptor 380 can then be completely removed, leaving only the universal anterior cutting guide adaptor 380 pinned in place on the femur, the plate portion 384 thereof being positioned exactly where the anterior cut is to be made. The standard anterior cutting guide block 382 corresponding to the particular implant being used is then simply slid onto the plate portion 384 of the universal anterior cutting guide adaptor 380, and pinned in place as shown in FIG. 20*b*. The universal anterior cutting guide adaptor 380 can then be removed from the femur, and the anterior cut can then be made.

The embodiments of the invention described above are intended to be exemplary only. The scope of the invention is therefore intended to be limited solely by the scope of the appended claims.

The invention claimed is:

1. A computer assisted total knee replacement surgery system comprising:
   a positioning block including a portion fastenable to a bone element and defining a reference surface thereon, the positioning block including a cutting tool guide operatively engageable with a cutting tool, the cutting tool guide being displaceable relative to the reference surface of said portion of the positioning block in at least three degrees of freedom, the three degrees of freedom comprising two rotational degrees of freedom and one translation degree of freedom;
   the positioning block including a trackable member in communication with the computer assisted surgery system, the computer assisted surgery system being operable to determine at least an orientation of the cutting tool guide of the positioning block relative to the bone element based on at least one of a position and orientation of the trackable member in space;
   the positioning block, in conjunction with the computer assisted surgery system, being operable to identify at least a desired orientation of the cutting tool guide relative to the bone element, such that at least one of the reference surface and the cutting tool guide is disposed in the desired orientation relative to the bone element whereby the cutting tool, guided by the cutting tool guide, is operable to create a cut in the bone element at the desired orientation; and a display for indicating when the desired orientation of the cutting tool guide is reached, wherein the display indicates actual orientation of the cutting tool guide and indicates when the desired orientation of the cutting tool guide is reached.

2. The system as defined in claim 1, further comprising means for determining and indicating where to fasten the positioning block on the bone element such that the positioning block is located in a desired position.

3. The system as defined in claim 1, wherein the positioning block is engageable to a polyaxial screw used to fasten the positioning block to the bone element.

4. The system as defined in claim 3, wherein the polyaxial screw comprises an engagement member permitting removable engagement with a screwdriver having a trackable member thereon, the trackable member being detectable by the computer assisted surgery system such that the screwdriver can be tracked, thereby permitting tracking of the bone screw during use.

5. The system as defined in claim1, wherein the positioning block is adjustable relative to the bone element in five degrees-of-freedom such that the positioning block is selectively adjustable into a desired position.

6. The system as defined in claim 1, wherein the trackable member includes a detectable element that can be located and tracked in three dimensional space by the computer assisted surgery system.

7. The system as defined in claim 1, wherein the positioning block comprises at least one of: a first cutting surface; and means for engaging the cutting tool guide having at least a second cutting positioning surface.

8. The system as defined in claim 1, wherein the computer assisted surgery system determines and indicates the location of the cutting tool guide relative to a portion of the positioning block adapted to be fastened to the bone element, such that the cutting tool guide is positioned in the desired orientation.

9. The system as defined in claim 8, wherein the cutting tool guide is selectively translatable relative to the positioning block along a platform, and the display indicates an exact location at which to fix the cutting tool guide such that the cutting tool guide is located in a selected position.

* * * * *